(12) United States Patent
Cao et al.

(10) Patent No.: US 11,266,497 B2
(45) Date of Patent: Mar. 8, 2022

(54) LOW GRADIENT PROSTHETIC HEART VALVES

(71) Applicant: Edwards Lifesciences Corporation, Irvine, CA (US)

(72) Inventors: Hengchu Cao, Irvine, CA (US); Wei Sun, South Windsor, CT (US)

(73) Assignee: Edwards Lifesciences Corporation, Irvine, CA (US)

(*) Notice: Subject to any disclaimer, the term of this patent is extended or adjusted under 35 U.S.C. 154(b) by 174 days.

(21) Appl. No.: 16/672,381

(22) Filed: Nov. 1, 2019

(65) Prior Publication Data

US 2020/0060812 A1 Feb. 27, 2020

Related U.S. Application Data

(60) Division of application No. 15/403,423, filed on Jan. 11, 2017, now Pat. No. 10,463,480, which is a continuation of application No. 13/105,469, filed on May 11, 2011, now Pat. No. 9,554,901.

(60) Provisional application No. 61/334,069, filed on May 12, 2010.

(51) Int. Cl.
*A61F 2/24* (2006.01)
*A61L 27/36* (2006.01)

(52) U.S. Cl.
CPC .......... *A61F 2/2412* (2013.01); *A61F 2/2418* (2013.01); *A61L 27/3625* (2013.01); *A61F 2210/0014* (2013.01); *A61F 2220/0075* (2013.01)

(58) Field of Classification Search
CPC ......... A61F 2/24; A61F 2/2412; A61F 2/2418
See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,755,823 A | 9/1973 | Hancock |
| 3,839,741 A | 10/1974 | Haller |

(Continued)

FOREIGN PATENT DOCUMENTS

| | | |
|---|---|---|
| EP | 0096721 A4 | 2/1985 |
| EP | 0143246 A3 | 2/1986 |

(Continued)

OTHER PUBLICATIONS

International Search Report from corresponding PCT application No. PCT/US2011/036315 dated Jan. 18, 2012.

(Continued)

*Primary Examiner* — Matthew W Schall
(74) *Attorney, Agent, or Firm* — Guy Cumberbatch

(57) ABSTRACT

A low pressure gradient prosthetic heart valve for implant in a human. The valve includes a support frame with undulating inflow cusps and outflow commissure posts to which flexible leaflets attach and coapt in a flow area. The commissure posts angle outward in a neutral state to widen the outflow orifice area. Also, the leaflets are designed to fit within the support frame and expand outward in a valve open state without creating a shelf or belly that would restrict flow.

20 Claims, 15 Drawing Sheets

(56) References Cited

U.S. PATENT DOCUMENTS

| | | |
|---|---|---|
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,291,420 A | 9/1981 | Reul |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,501,030 A | 2/1985 | Lane |
| 4,506,394 A | 3/1985 | Bedard |
| 4,510,628 A | 4/1985 | Kolff |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,283,127 B1 | 9/2001 | Sterman et al. |
| 6,283,994 B1 | 9/2001 | Moe et al. |
| 6,283,995 B1 | 9/2001 | Moe et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,328,763 B1 | 12/2001 | Love et al. |
| 6,371,983 B1 | 4/2002 | Lane |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,558,418 B2 | 5/2003 | Carpentier et al. |
| 6,562,069 B2 | 5/2003 | Cai et al. |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,719,789 B2 | 4/2004 | Cox |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |

(56) References Cited

U.S. PATENT DOCUMENTS

| | | |
|---|---|---|
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,018,404 B2 | 3/2006 | Holmberg et al. |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 8,845,720 B2 | 9/2014 | Conklin |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0128707 A1 | 9/2002 | Kavteladze et al. |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209671 A1 | 9/2005 | Ton et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0271844 A1 | 12/2005 | Mapes et al. |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0246888 A1 | 11/2006 | Bender et al. |
| 2006/0259136 A1 | 11/2006 | Nguyen et al. |
| 2006/0271064 A1 | 11/2006 | Agnew |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |

(56) References Cited

U.S. PATENT DOCUMENTS

| | | |
|---|---|---|
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0228264 A1 | 9/2008 | Li et al. |
| 2008/0319543 A1 | 12/2008 | Lane |
| 2009/0036903 A1 | 2/2009 | Ino et al. |
| 2009/0112309 A1 | 4/2009 | Jaramillo et al. |
| 2009/0192599 A1 | 7/2009 | Lane et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2012/0143324 A1 | 6/2012 | Rankin et al. |

FOREIGN PATENT DOCUMENTS

| | | |
|---|---|---|
| EP | 0084395 B1 | 8/1986 |
| EP | 0125393 B1 | 12/1987 |
| EP | 0179562 B1 | 7/1989 |
| EP | 1171059 A1 | 1/2002 |
| GB | 2056023 A | 3/1981 |
| GB | 2 069 843 A | 9/1981 |
| GB | 2254254 A | 10/1992 |
| GB | 2 279 134 A | 12/1994 |
| SU | 1116573 A1 | 7/1985 |
| WO | 8900084 A1 | 1/1989 |
| WO | 9115167 A1 | 10/1991 |
| WO | 9201269 A1 | 1/1992 |
| WO | 9213502 A1 | 8/1992 |
| WO | 9219184 A1 | 11/1992 |
| WO | 9219185 A1 | 11/1992 |
| WO | 9517139 A1 | 6/1995 |
| WO | 20199528899 A1 | 11/1995 |
| WO | 201996040006 A1 | 12/1996 |
| WO | 9709933 A1 | 3/1997 |
| WO | 9709944 A1 | 3/1997 |
| WO | 9727799 A1 | 8/1997 |
| WO | 9741801 A1 | 11/1997 |
| WO | 9742871 A1 | 11/1997 |
| WO | 9806329 A1 | 2/1998 |
| WO | 9911201 A2 | 3/1999 |
| WO | 9915112 A1 | 4/1999 |
| WO | 9951169 A1 | 10/1999 |
| WO | 0032105 A1 | 6/2000 |
| WO | 0040176 A1 | 7/2000 |
| WO | 0060995 A2 | 10/2000 |
| WO | 0062716 A1 | 10/2000 |
| WO | 2006086135 A2 | 8/2006 |

OTHER PUBLICATIONS

Ionescu, M.I., "The Pericardial Xenograft Valve: Mode of Failure and Possible Remedial Developments," In: Bodnar E, Yacoub M, eds. Biologic and bioprosthetic valves. Yorke Medical Books, pp. 245-251, 1986.

B. Lee, et al., "Reconstruction of Trileaflet Heart Valve Leaflet Motion by Using Photogrammetry and Biquintic Finite Element Method", Biomedical Engineering Research Institute; 2003 Summer Bioengineering Conference, Jun. 25-29, Sonesta Beach Resort in Key Biscayne, Florida, pp. 1-7.

Jose R. Borrero, et al., "Mechanics of Prosthetic Heart Valves", Applications of Engineering Mechanics in Medicine, Ged. Dec. 2003; University of Puerto Rico, Mayaguez, pp. 1005-1006.

Wei Sun, et al., "Simulated Bioprosthetic Heart Valve Deformation Under Quasi-Static Loading", Journal of Biomechanical Engineering. Nov. 2005; vol. 127; pp. 905-914.

Wei Sun, et al., "Finite Element Implementation of a Generalized Fung-Elastic Constitutive Model for Planar Soft Tissues", Biomech Model Mechanobiol. Nov. 2005; 4(2-3): 190-9.

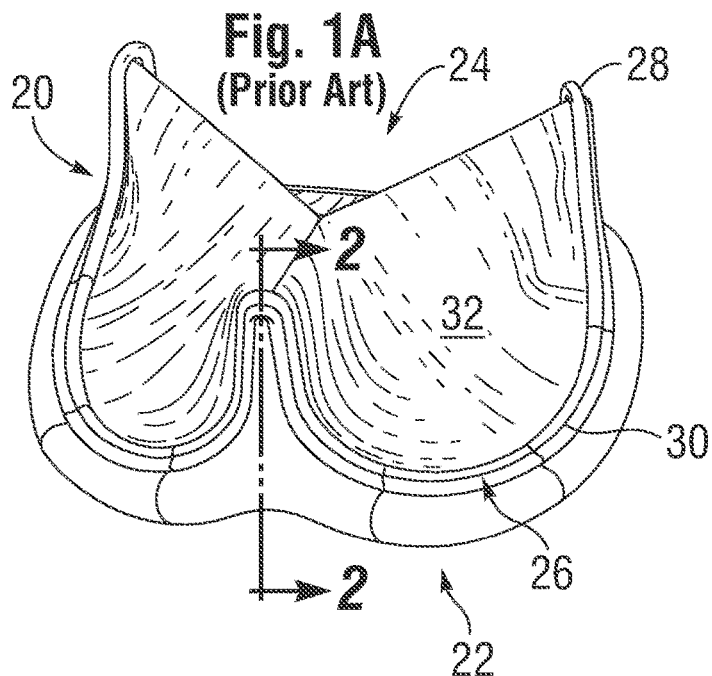
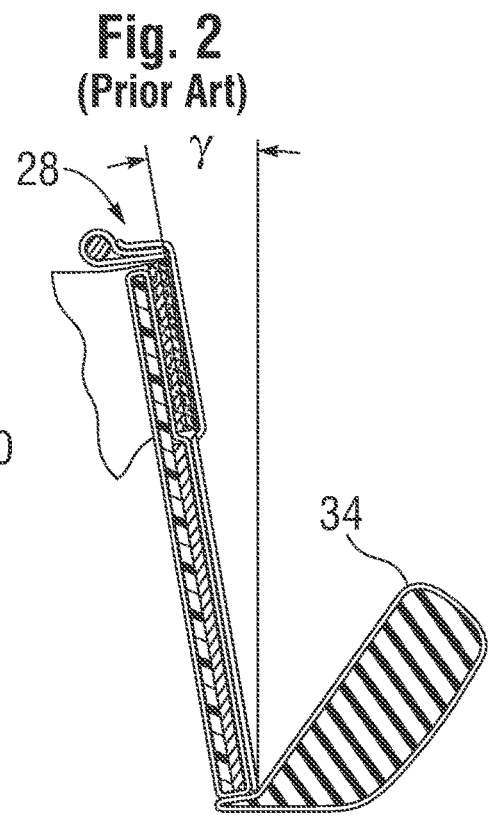
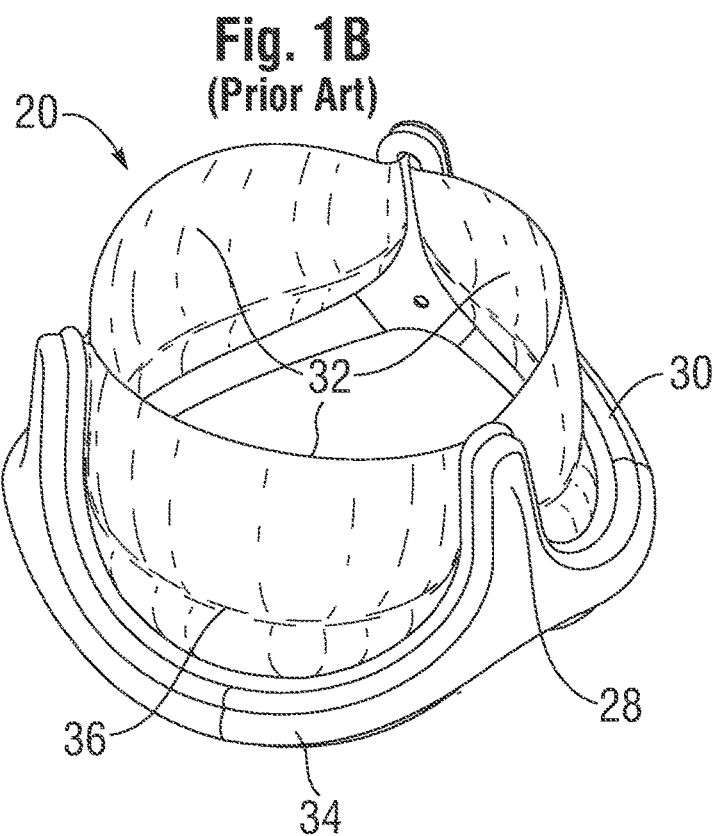

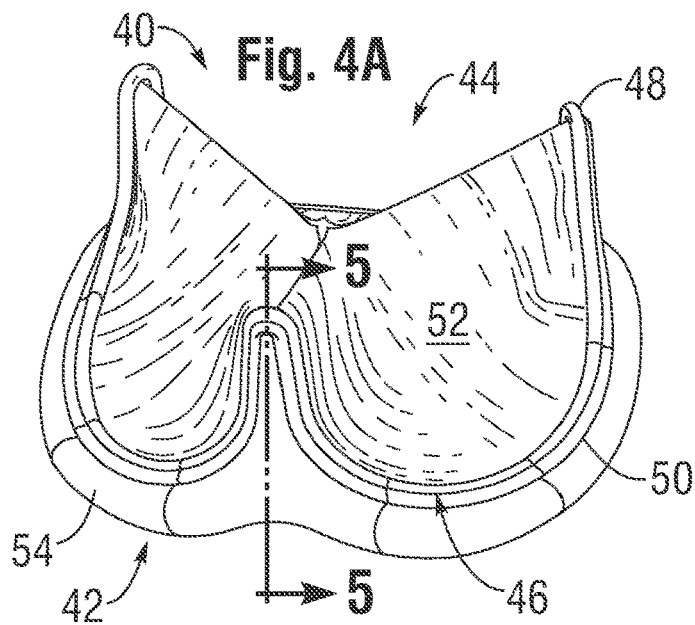
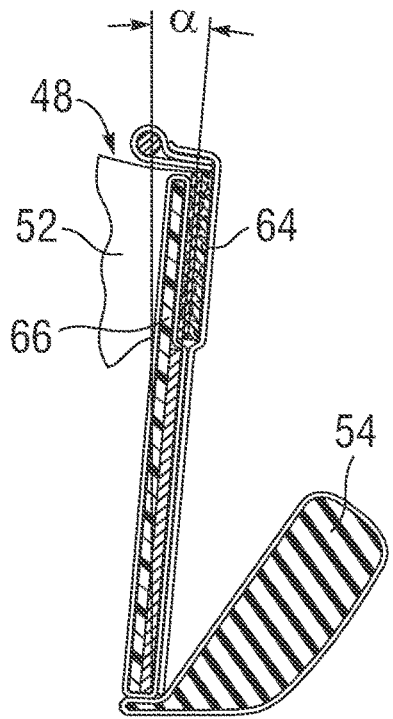
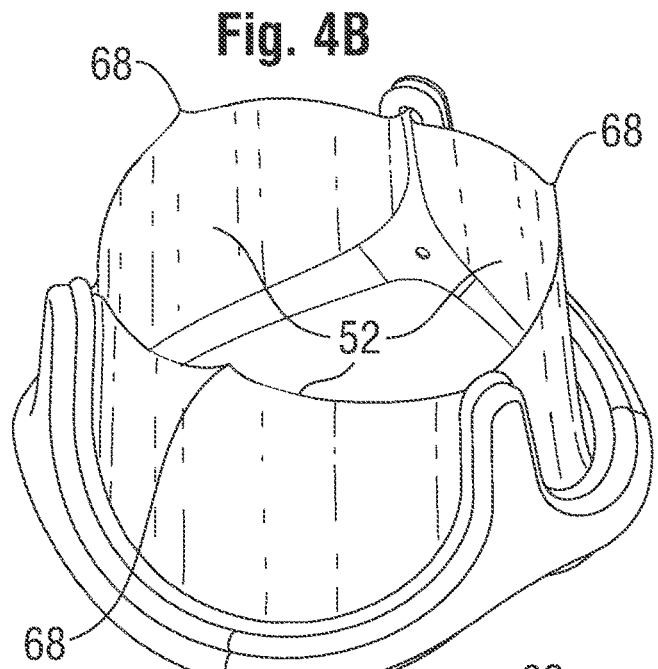
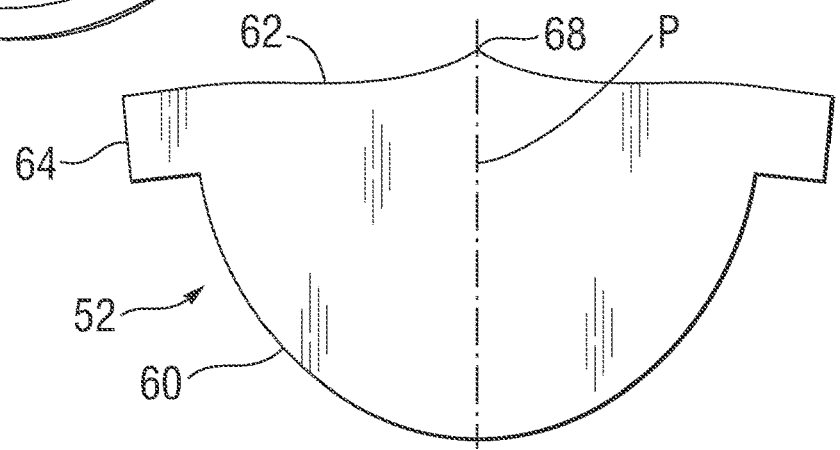

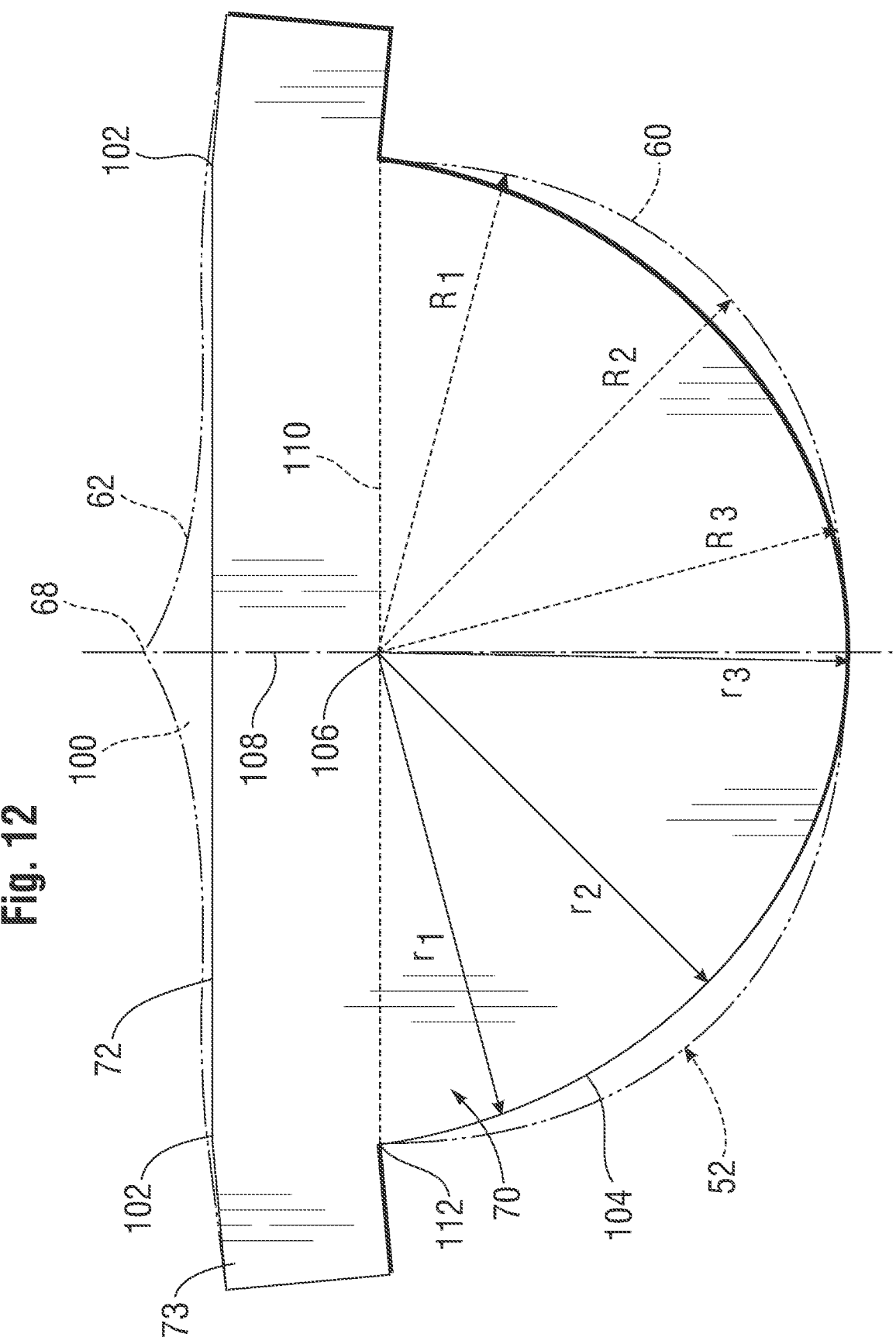

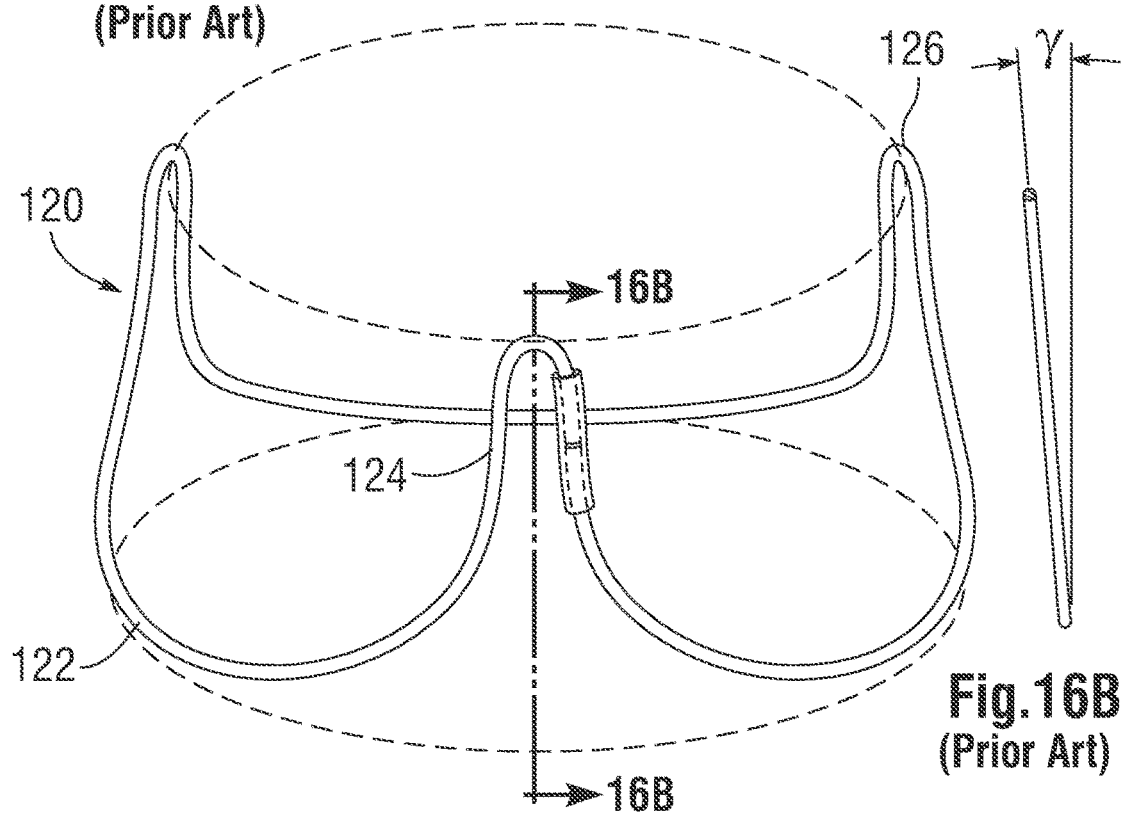
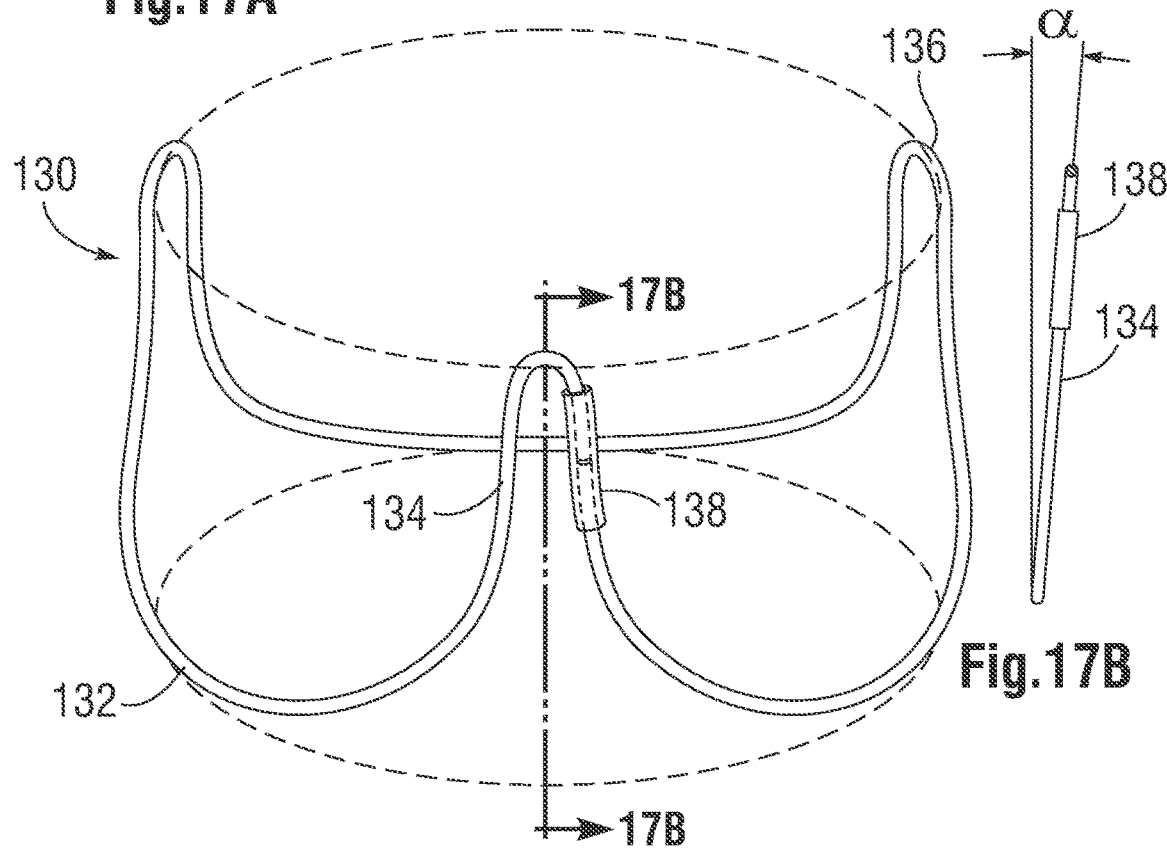

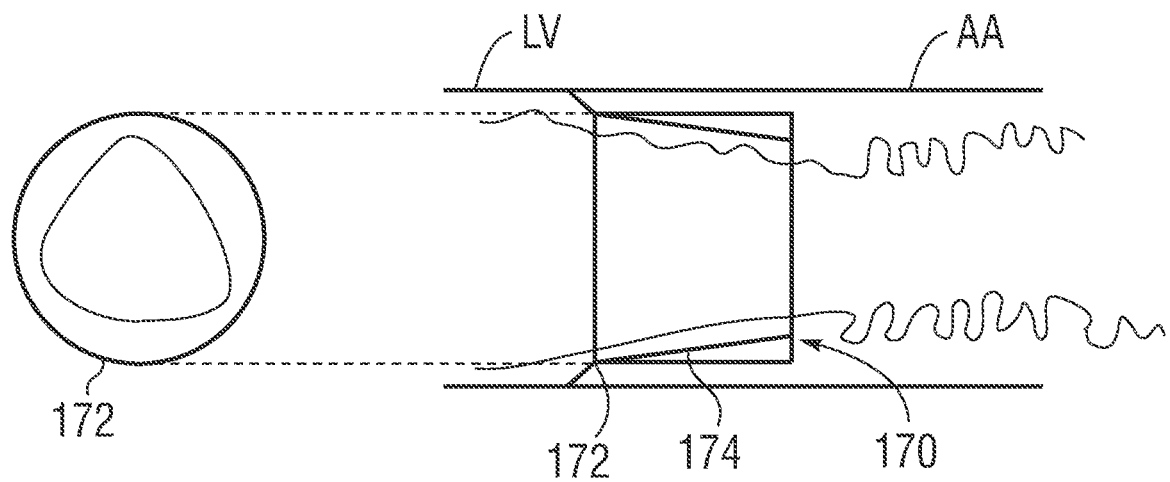
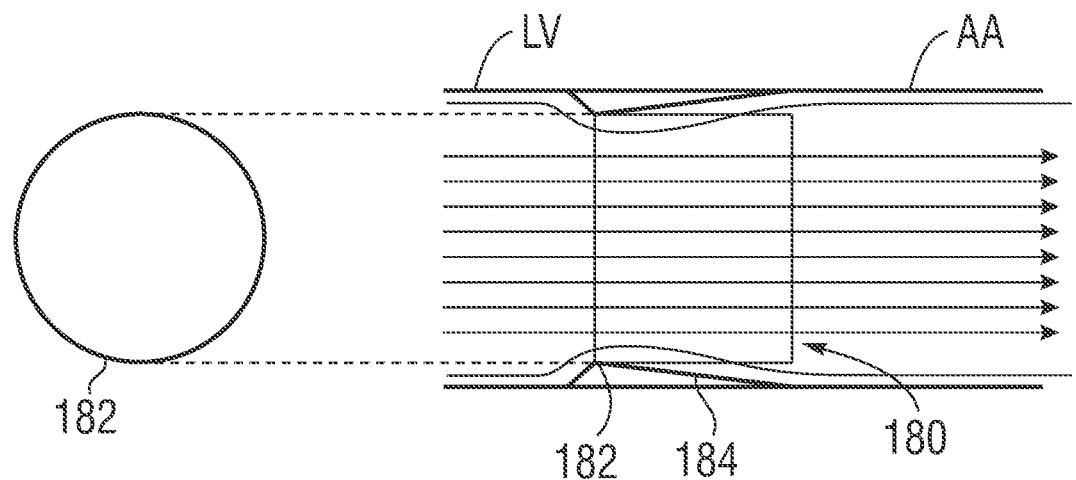

LOW GRADIENT PROSTHETIC HEART VALVES

CROSS REFERENCE TO RELATED APPLICATIONS

This application is a divisional of U.S. application Ser. No. 15/403,423, filed Jan. 11, 2017 and now U.S. Pat. No. 10,463,480, which a continuation of U.S. application Ser. No. 13/105,469, filed May 11, 2011 and now U.S. Pat. No. 9,554,901, which claims the benefit of U.S. Application No. 61/334,069, filed May 12, 2010, the entire disclosures all of which are incorporated by reference for all purposes.

FIELD OF THE INVENTION

The present invention relates to a prosthetic heart valve having a reduced pressure gradient for enhanced flow and, more particularly, to a flexible leaflet valve with modified stent and leaflet structure that reduces the pressure drop therethrough.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Recent statistics show that valvular heart disease is responsible for nearly 20,000 deaths each year in the United States, and is a contributing factor in approximately 42,000 deaths. Worldwide, approximately 300,000 heart valve replacement surgeries are performed annually, and about one-half of these patients received so-called mechanical heart valves, which are composed of rigid, synthetic materials. The remaining patients received bioprosthetic heart valve replacements, which utilize biologically derived tissues for flexible fluid occluding leaflets. In general, bioprosthetic valve replacements have good hemodynamic performance and do not require the anticoagulation therapy necessary for mechanical heart valves. However, these bioprostheses sometimes fail as a result of calcification and mechanical damage.

Flexible leaflets used in heart valves are typically made from bioprosthetic homograft or xenograft materials. For example, the most successful bioprosthetic materials are whole porcine valves and separate leaflets made from bovine pericardium stitched together to form a tri-leaflet valve. In addition, flexible leaflets formed of polymeric, fiber-reinforced, and other synthetic materials have been proposed. The most common bioprosthetic valve construction includes three leaflets mounted around a peripheral support structure with free edges that project toward an outflow direction and meet or coapt in the middle of the flowstream.

Aortic stenosis is abnormal narrowing of the aortic valve. A number of conditions cause disease resulting in narrowing of the aortic valve. When the degree of narrowing becomes significant enough to impede the flow of blood from the left ventricle to the arteries, heart problems develop.

Aortic stenosis is characterized by a significantly higher than normal pressure gradient across the aortic valve. Studies have demonstrated that 85% of patients with surgically untreated aortic stenosis die within 5 years after the onset of symptoms. It follows that an important characteristic of a replacement aortic valve is minimal aortic pressure gradient, especially in symptomatic patients. Many aortic prosthetic valve manufacturers place emphasis on the placement of the prosthesis (sub-annular, intra-annular and supra-annular) in order to draw attention to the importance of implanting a prosthesis with the largest possible effective orifice area. Supra-annular placement (where the sewing cushion lies above the aortic annulus) is often preferred because usually a valve with a larger internal orifice diameter can be implanted. In patients with small aortic roots, either due to anatomy, physical stature, or severe calcification, only the smallest-sized valves (e.g., 19 mm) may be used. Sometimes an even smaller valve would be desirable, but valves smaller than 19 mm are not commercially available. Moreover, even with a supra-annular implant, the smallest prostheses may result in pressure gradients of between 20 and 60 mm Hg and clinically significant aortic stenosis. In all sizes, but in particular with small valves, a reduced gradient that approaches a human native heart valve is preferred and thought to improve long term patient survival rates.

Typical bioprosthetic heart valves have a rigid structure that supports the flexible leaflets. The constant valve seat shape helps ensure reliable closure of the leaflets. Many such artificial valves have circular suture rings made rigid by a metal insert so that they cannot adjust to the natural changes in size of the aorta which surrounds them after the implantation. A common design is a suture ring around a stent structure with three, equiangularly-spaced projecting legs or commissures which extended substantially parallel to one another in the axial direction of the ring. The stent supports three, separate leaflet cusps, and the suture ring interconnects the bottom portions of the projecting legs thereby preventing free, radial movement thereof. To overcome these disadvantages, flexible artificial heart valves have been proposed, such as in U.S. Pat. No. 4,291,420 to Reul, and U.S. Pat. No. 6,558,418 to Carpentier, et al. Though these designs are promising, the conventional rigid circular base remains the dominant surgeon preference.

Bioprosthetic heart valves made by Edwards Lifesciences of Irvine, Calif. have demonstrated excellent durability and hemodynamic performance for a majority of patients without the need for anti-coagulation therapy, which is usually required for mechanical heart valves. In particular, Edwards' bioprostheses such as the PERMOUNT line of valves with pericardial leaflets offer superior hemodynamic performance compared to those with porcine leaflets.

Another issue for some patients with low cardiac output or anticipated recovery difficulty is a small amount of regurgitation associated with some bioprosthetic valves. The three flexible leaflets in a typical bioprosthetic valve meet or coapt within the flow orifice but tend to separate at their convergence in the very middle, which allows a small amount of regurgitation. Though most patients tolerate such minor regurgitation, any increased demand on the heart is problematic for very sick patients and may lead to a slower recovery.

In view of actual and perceived drawbacks associated with current bioprosthetic heart valves, a valve across which there is a minimal pressure gradient and reduced regurgitation is desirable.

SUMMARY OF THE INVENTION

The present application provides a low pressure gradient prosthetic heart valve for implant in a human. The valve includes a support frame with undulating inflow cusps and outflow commissure posts to which flexible leaflets attach and coapt in a flow area. The commissure posts angle outward in a neutral state to widen the outflow orifice area. Also, the leaflets are designed to fit within the support frame and expand outward in a valve open state without creating a shelf or belly that would restrict flow.

One embodiment of a low pressure gradient prosthetic heart valve comprises a support frame including an undulating leaflet attachment edge with alternating arcuate inflow cusps and arcuate outflow commissures ending in tips. The leaflet attachment edge in a relaxed state of the support frame circumscribes a flow volume having a central axis, the flow volume having a maximum flow orifice area perpendicular to the central axis limited by the inflow end of the support frame. A plurality of flexible leaflets attach to the support frame and extending inward toward the axis. Each leaflet has an arcuate cusp edge that conforms to a corresponding support frame cusp and attaches therealong between adjacent commissures, and a free edge that coapts with the free edges of the other leaflets to provide one way flow through the valve. When the valve opens, the free edges of the leaflets move outward toward the generally tubular shape described by the support frame from fluid flow in an outflow direction and corresponding fluid pressures. Finally, each commissure of the relaxed support frame angles radially outward so as to provide an outflow orifice area greater than the maximum flow orifice area and induce laminar flow through the valve. The radially outward angle made by each commissure is preferably $\alpha=4\pm3°$.

Another embodiment of the low pressure gradient prosthetic heart valve comprises a support frame including an undulating leaflet attachment edge with alternating arcuate inflow cusps and arcuate outflow commissures, the leaflet attachment edge circumscribing a flow volume having a central axis, and the flow volume having a maximum flow orifice area perpendicular to the central axis limited by the inflow end of the support frame. A plurality of flexible leaflets attach to the support frame and extend inward toward the axis. Each leaflet has an arcuate cusp edge that conforms to a corresponding support frame cusp and attaches therealong between adjacent commissures, and a free edge that coapts with the free edges of the other leaflets to provide one way flow through the valve. When the valve opens, the free edges of the leaflets move outward toward the flow volume described by the support frame from fluid flow in an outflow direction and corresponding fluid pressures. Further, each leaflet has a size and is attached to the corresponding support frame cusp such that when the valve opens the leaflets spread outward to provide an outflow orifice area that is no less than the maximum flow orifice area. The support frame desirably has a relaxed state and each commissure of the relaxed support frame is angled radially outward so as to provide an outflow orifice area greater than the maximum flow orifice area and induce laminar flow through the valve.

In either version of the aforementioned low pressure gradient prosthetic heart valves, the inflow cusps of the support frame reside in an inflow plane within which is defined an inflow diameter $\Phi_i$ circumscribed by the nadirs of the cusps, and the commissures of the support frame have an axial height H from the inflow plane to their tips that satisfies the following relationship:

$$\frac{H}{\Phi_i} = 0.5 \pm .1$$

Also, the heart valve leaflets may have a coaptation point along the central axis where all three leaflets meet upon valve closing, and a coaptation height h from the inflow plane to the coaptation point that satisfies the following relationship:

$$\frac{h}{H} = 0.7 \pm .1$$

In any of the valves defined herein, the support frame may comprise an elongated rod-like member made out of an elastic material. For instance, the support frame may be formed as a continuous piece of Nitinol with no breaks or crimp. In one embodiment, wherein the commissures of the support frame each include an upstanding bar and a series of through holes therein that provide anchor points for other elements of the heart valve. Also, each leaflet preferably has opposed attachment tabs disposed between its arcuate cusp edge and its free edge. Each leaflet has a central area subject to stress when secured within a surrounding heart valve support frame, wherein the leaflet is symmetric about a central plane and the arcuate cusp edge may be defined by a complex curve of multiple radii. The complex curve has a smaller radius that gradually decreases on both sides away from the central plane, reaches a maximum at about 45° angle from the central axis, and gradually increases to two corners where the two ends of the arcuate cusp edge meet the attachment tabs.

In accordance with another aspect of the application, a leaflet for a low pressure gradient prosthetic heart valve comprises a flexible leaflet having an arcuate cusp edge opposite a free edge and opposed attachment tabs therebetween. The leaflet has a central area subject to stress when secured within a surrounding heart valve support frame, and is symmetric about a central midplane. The arcuate cusp edge is defined by a complex curve of multiple radii, the complex curve having its smallest radius on the central midplane that gradually increases on both sides away from the central plane, reaches a maximum at about 45° angle from the central axis, and then gradually decreases to two corners where the two ends of the arcuate cusp edge meet the attachment tabs. The free edge may diverge above a straight line drawn between the side tabs to form a supplemental strip of leaflet material that gradually widens as it progresses inward from the tabs until it forms a plateau for a majority of its length, and then rapidly widens in converging curves that lead to an apex on the vertical midplane. Alternatively, the free edge diverges above a straight line drawn between the side tabs to form a supplemental strip of leaflet material shaped generally as a triangle with an apex on the vertical midplane. The leaflet is desirably cut from bovine pericardium.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIG. 1A is a perspective view of a bioprosthetic heart valve of the PRIOR ART shown from an outflow end view with the leaflets closed, and FIG. 1B is from the outflow end and rotated about 30° with the leaflets open;

FIG. 2 is a radial sectional view through one commissure post of the heart valve of FIG. 1A;

FIG. 4A is a perspective view of an exemplary bioprosthetic heart valve of the present application shown from an outflow end view with the leaflets closed, and FIG. 4B is from the outflow end and rotated about 30° with the leaflets open;

FIG. 5 is a radial sectional view through one commissure post of the exemplary heart valve of FIG. 4A;

FIG. 6A is a plan view of a flexible leaflet of the present application that can be incorporated into the bioprosthetic heart valve of FIG. 4A;

FIG. 12 is a plan view of a flexible leaflet of the PRIOR ART with a flexible leaflet of the present application superimposed in phantom thereover, with pertinent "radial" dimensions from a central point to a cusp edge indicated;

FIG. 13A is a perspective view of isolated flexible leaflets of a bioprosthetic heart valve of the PRIOR ART in the open position, while

FIG. 16A is a perspective view of a wireform or support frame for bioprosthetic heart valves of the PRIOR ART, and FIG. 16B is a radial sectional view through one commissure of the support frame showing an inward angle thereof;

FIG. 17A is a perspective view of a wireform or support frame for a bioprosthetic heart valve of the present application, and FIG. 17B is a radial sectional view through one commissure of the support frame showing potential angles thereof;

FIG. 20 schematically shows blood flow through a prosthetic heart valve of the prior art that constricts and creates turbulent flow;

FIG. 21 schematically shows blood flow through a prosthetic heart valve of the present application that expands and creates laminar, low gradient flow;

DETAILED DESCRIPTION OF THE PREFERRED EMBODIMENTS

Figure 3A:
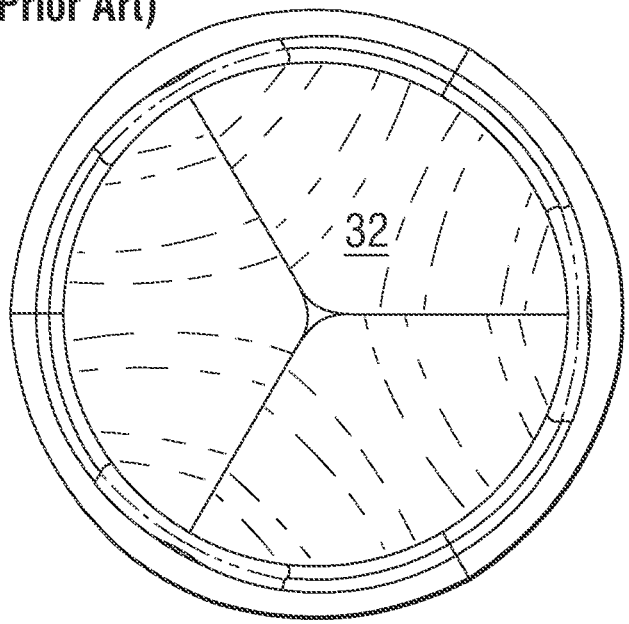
FIGS. 3A-3C are top plan, side elevational, and rotated perspective views of the bioprosthetic heart valve of FIG. 1A.
Figure 3B:
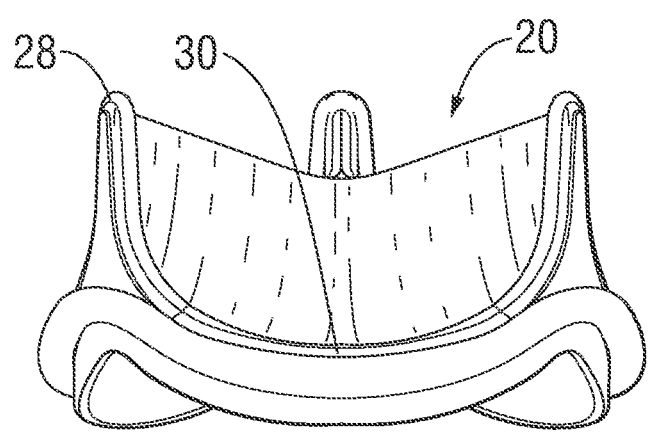
Figure 3C:
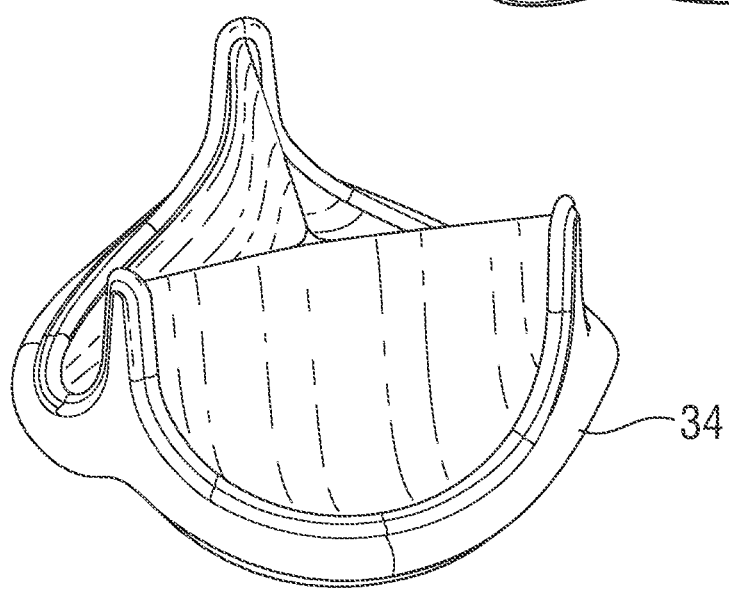

The present application describes certain principles that may be used in conjunction or separately for fabricating flexible leaflet prosthetic heart valves to reduce the pressure gradient of blood through the valve orifice. As general statements of benefits obtained from such a valve: the valve should open properly upon forward flow with minimal gradient; the valve should close properly and completely upon reverse flow with little regurgitation; the support structure (e.g., wireform) of the valve should be able to withstand the fatigue stress during a large number of the valve open/close cycles and maintain structural integrity; and the flexible leaflets should withstand the structural stress and maintain the structural function of opening and closing without calcification or structural deterioration.

The desire for these attributes is not necessarily new in the field of prosthetic heart valve design, but valves constructed based on the principles described herein improve on each, in particular by minimizing the pressure gradient across the valve. It should be understood that the characteristics of heart valves expressed herein may be implemented in a variety of different flexible leaflet valves. For example, though three- or tri-leaflet valves are the most common and most studied, only two or a greater number of leaflets may also be used. Also, the support frame, or structural skeleton, for the flexible leaflets may take a variety of forms in addition to those illustrated and described herein. The valve support frame may be relatively dimensionally stable, or configured to be collapsible for minimally-invasive delivery. Finally, materials and fabrication techniques may vary while still conforming any valve to the described desirable principles. In summary, the present application encompasses many valves that include one or more of these variable aspects, only limited by the appended claims.

As used herein, a "neutral position" or a "neutral configuration" means a configuration of a valve and/or a frame when the respective valve and/or frame is at-rest (e.g., still) and free from externally applied loads (e.g., pressure gradients through the valve, forces applied by retaining and/or delivery devices to retain the valve in a collapsed configuration).

A prosthetic heart valve 20 of the prior art shown in FIGS. 1A/1B, 2, and 3A/3C includes an inlet end 22 and an outlet end 24 separated along a vertical flow axis through the middle of the valve. A cloth-covered frame assembly or support frame 26 defines a periphery and flow orifice of the valve and includes commissure posts 28 that project generally axially in the outflow direction separated by arcuate cusps 30 that curve in the inflow direction. Three flexible leaflets 32 couple to the frame 26 and extend inward therefrom. The leaflets 32 attach along an undulating line that follows the commissure posts 28 and cusps 30. A suture-permeable sewing ring 34 surrounds the inflow end of the valve 20 and, as shown, features a non-planar peripheral shape which undulates upward a short distance in the vicinity of the three commissure posts 28. A planar sewing ring 34 may also be used.

The leaflets 32 may be provided by a whole porcine valve, but are preferably formed individually from bioprosthetic material such as bovine pericardium. It should be noted that a number of advantages of the present application are independent of the type of flexible leaflet, though the maximum benefit will be obtained by using sheets of bovine pericardium trimmed to particular sizes and shapes, as will be explained. Although not presently used in commercial valves, synthetic material may also be used for the leaflets, and the term, "flexible leaflets" is meant to include such other materials.

FIG. 1A shows the bioprosthetic heart valve 20 with the leaflets 32 closed, and FIG. 1B shows the leaflets open. As will be explained in more detail below, typical valves of the prior art have relatively floppy leaflets 32 that generally effectively coapt or meet in the flow orifice during the back flow portion of the flow cycle, as in FIG. 1A, and spread apart in the forward flow portion of the flow cycle, as in FIG. 1B. Due to the excess material of the leaflets 32, each leaflet sags somewhat inward when the valve is open to form a crease or shelf 36 near its mid-point. These shelves 36 extend inward beyond the generally circular orifice defined at the inflow end 22. Furthermore, as seen in FIG. 2, the commissure posts 28 tilt somewhat inwardly by an angle $\gamma$ relative to the central flow axis from their inflow to their outflow ends so as to define a surface of revolution that surrounds a converging conical volume. The angle $\gamma$ typically is equal to about 10°. This arrangement provides a flow constriction wherein the size of the orifice provided by the posts 28 and intermediate leaflets 32 in the valve open state, as in FIG. 1B, is smaller than the generally circular orifice defined at the inflow end 22. The combination of the generally conical flow column and inward shelves or pockets created by the floppy leaflets introduces flow restrictions that increase the fluid pressure gradient through the valve as opposed to a smooth cylinder, or idealized pipe flow.

FIGS. 4A/4B and 5 show an exemplary bioprosthetic heart valve 40 of the present application which is constructed in much the same way as the valve of the prior art above. Namely, the valve 40 includes an inlet end 42 and an outlet end 44 separated along a vertical flow axis through the middle of the valve. A cloth-covered frame assembly or support frame 46 defines a periphery and flow orifice of the valve and includes commissure posts 48 that project generally axially in the outflow direction separated by arcuate cusps 50 that curve in the inflow direction. Three flexible leaflets 52 couple to the frame 46 and extend inward therefrom. The leaflets 52 attach along an undulating line that follows the commissure posts 48 and cusps 50. A suture-permeable sewing ring 54 surrounds the inflow end of the valve 40 and, as shown, features a non-planar peripheral shape which undulates upward a short distance in the vicinity of the three commissure posts 48. A planar sewing ring 54 may also be used.

FIG. 5 shows a representative one of the commissure posts 48 tilted somewhat outwardly relative to the central flow axis by an angle $\alpha$ toward their outflow ends so as to define a surface of revolution that surrounds a diverging conical volume. The angle $\alpha$ is desirably about 4°±3°, and is more preferably at least 4°. This arrangement provides a flow relaxation wherein the size of the orifice provided by the posts 48 and intermediate leaflets 52 in the valve open state (as in FIG. 4B) is larger than the generally circular orifice defined at the inflow end 42.

It should be noted that though the commissure posts 48 of the valve lean slightly outward when the valve is in a neutral configuration, the posts 48 are cantilevered upward from the inflow end of the valve, as the sewing ring 54 provides the structural anchor to the surrounding anatomy. Consequently, fluid forces tend to bend or flex the posts 48 from this neutral position. For example, an aortic valve closes during diastole, and the outlet end 44 can contract such that the commissure posts 48 lean inward from the neutral position to define a diameter, $D_{diastole}$. Conversely, during systole, the valve opens and the posts 48 revert back to their neutral positions or even bow outward somewhat to define a diameter, $D_{systole}$, wherein $D_{diastole}$ is slightly less than $D_{systole}$. Typically, the pressure gradient across the valve during systole is small enough (e.g., less than 10 mm Hg in some embodiments) that the commissure posts 48 remain in the neutral configuration, which is thus the systolic diameter $D_{systole}$.

Since the cantilevered structure of the support frame 46 preferably leans radially outward in an undeformed, neutral position, a larger outlet orifice is provided for the valve and a lower pressure gradient within a fluid passing through the valve. However, this outwardly leaning support frame 46 can obstruct access to the sewing ring 54 when the valve is in a neutral position. Therefore, the outwardly leaning cantilevered support structure may be flexed radially inward of the valve sewing ring during implantation, providing convenient access to the sewing ring 54.

Such inwardly and/or outwardly leaning, neutrally positioned commissure posts 48, when incorporated into an assembled prosthetic valve can provide improved hemodynamics through the valve. In other words, the extent to which the commissure posts 48 lean inwardly or outwardly in the neutral position (and/or implanted neutral configuration) can be adjusted, together with the leaflet design (described below), to obtain desired pressure gradients through the valve throughout the cardiac cycle when the valve is implanted.

FIG. 6A is a plan view of one of the three separate flexible leaflets 52 incorporated into the valve 40 of FIG. 4A. As mentioned, the leaflet 52 may be formed from a sheet of bovine pericardium, though other biomaterials and even synthetics are contemplated. Each leaflet 52 is desirably symmetric about a vertical midplane P that bisects an arcuate cusp edge 60 and an opposite free edge 62. The cusp edge 60 secures along a cusp 50 of the support frame 46 and terminates on either end in a pair of oppositely directed tabs 64. The tabs 64 anchor to the upper end of adjacent commissure posts 48, and preferably pass through adjacent rods of a stent post 66 and then wrap around and connect to each other outside of the stent post, such as seen in FIG. 5. This technique helps reduce localized stresses on the points of attachment of the leaflet at the upper end of the support frame 46 where the tensile forces are the largest.

Figure 11:
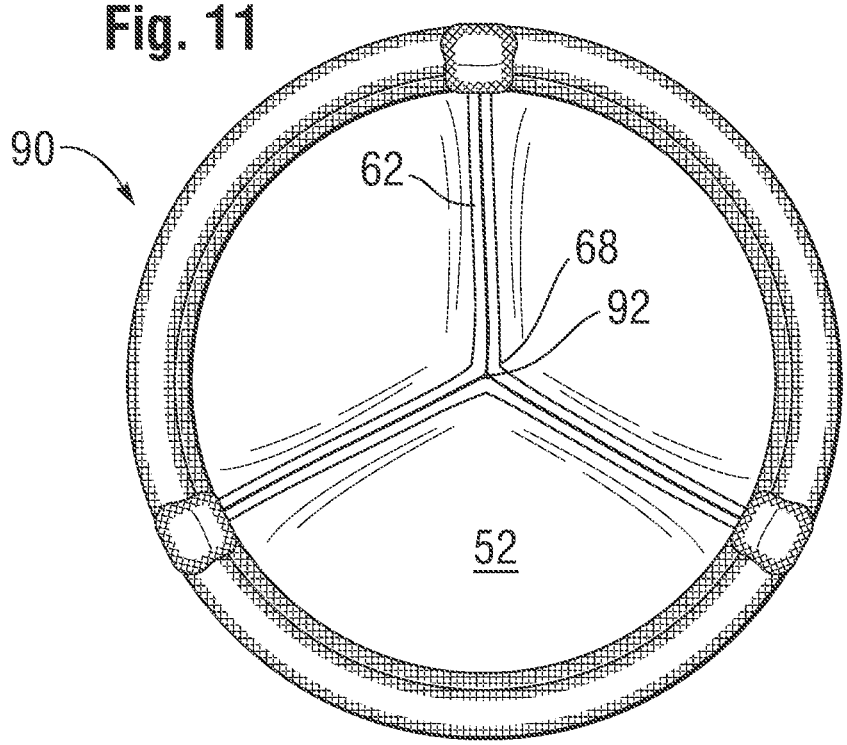
FIG. 11 is a top plan view of a bioprosthetic heart valve having three of the flexible leaflets shown in FIG. 6A in the closed position illustrating a reduced central aperture formed thereby.

The free edge 62 includes a contoured shape that helps reduce regurgitation. In particular, the free edge 62 extends generally radially inward to about halfway to the plane of symmetry, and then gently curves upward, or away from the cusp edge 60, to form a pointed apex 68. The three apices 68 are also seen in the valve perspective of FIG. 4B when the leaflets are open. These upwardly pointed apices 68 help close a small aperture that naturally forms between the three leaflets along the flow axis, as seen in FIG. 11.

Figure 6B:
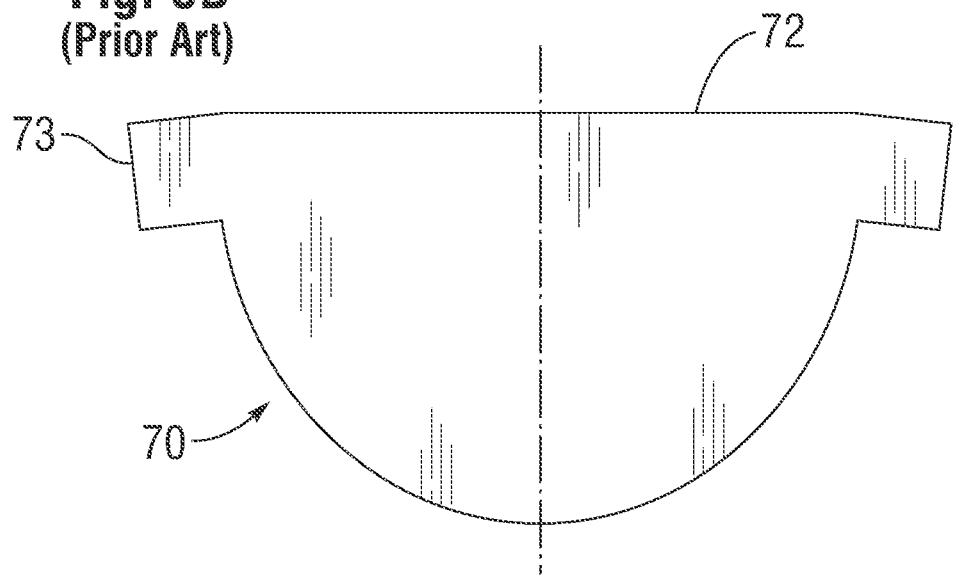
FIG. 6B is a plan view of a PRIOR ART flexible leaflet.
Figure 7:
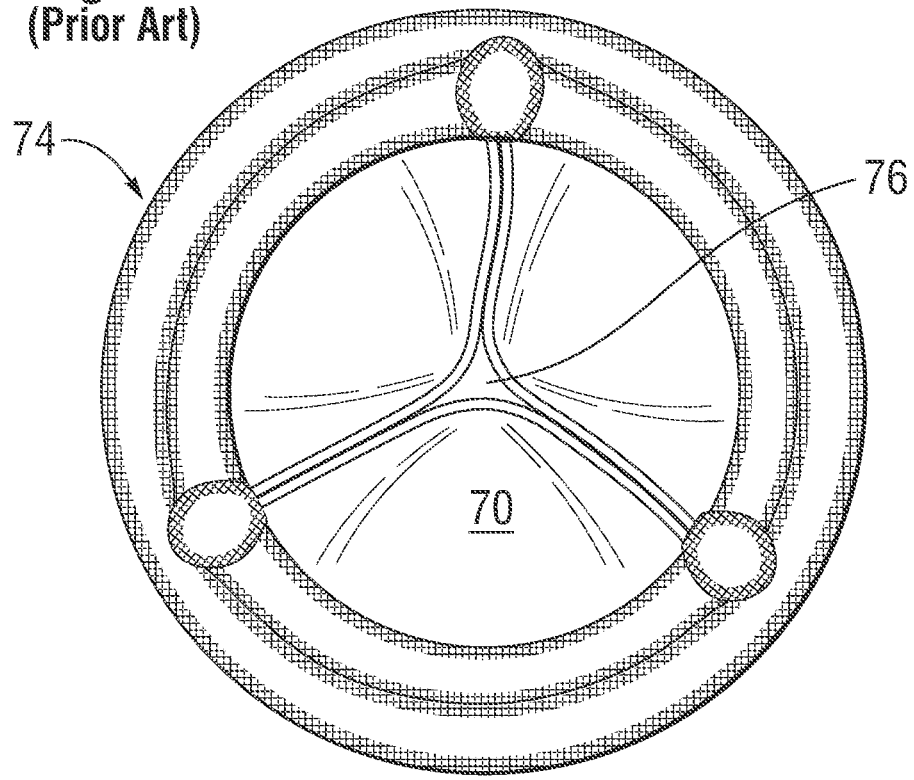
FIG. 7 is a top plan view of a bioprosthetic heart valve of the PRIOR ART having three of the flexible leaflets shown in FIG. 6B in the closed position illustrating a central aperture formed thereby that sometimes results in regurgitation.

In contrast, FIG. 6B is a plan view of a prior art flexible leaflet 70 and shows the lack of any contour along the free edge 72, which is relatively straight between the side tabs 73. FIG. 7 is a top plan view of a heart valve 74 of the prior art having three of the flexible leaflets 70 shown in FIG. 6B in the closed position, illustrating the central aperture 76 that may cause regurgitation.

Figure 8:
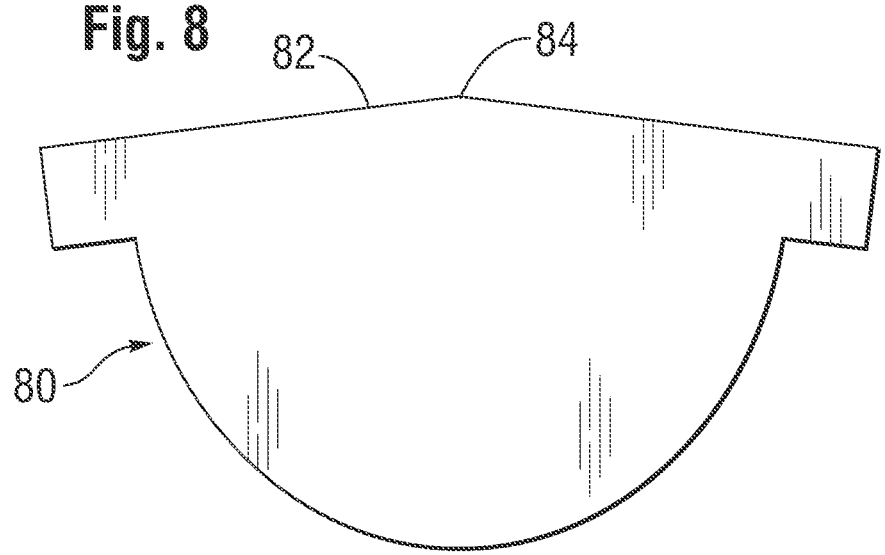
FIG. 8 is a plan view of an alternative flexible leaflet of the present invention having a free edge that tapers outward toward a central apex.
Figure 9:
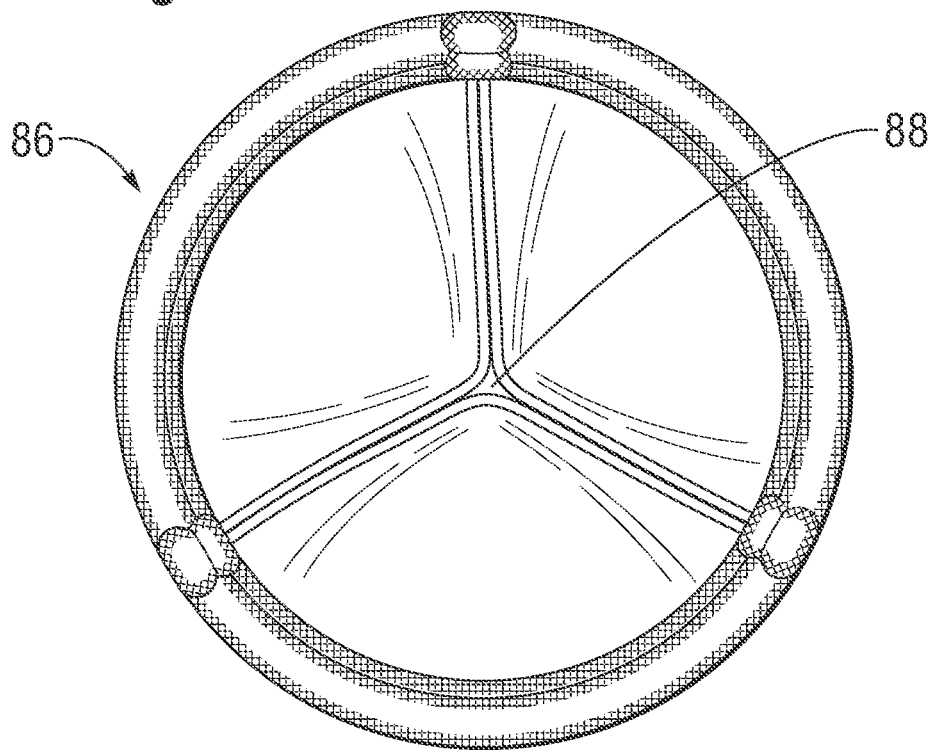
FIG. 9 is a top plan view of a bioprosthetic heart valve having three of the flexible leaflets shown in FIG. 8 in the closed position illustrating a reduced central aperture formed thereby.

FIG. 8 is a plan view of an alternative flexible leaflet 80 of the present invention having a free edge 82 that tapers toward a central apex 84. This taper also helps close the aforementioned aperture along the flow axis and reduce regurgitation. FIG. 9 is a top plan view of a heart valve 86 having three of the flexible leaflets 80 with taper free edges 82, and the reduced central aperture 88 formed thereby.

Figure 10:
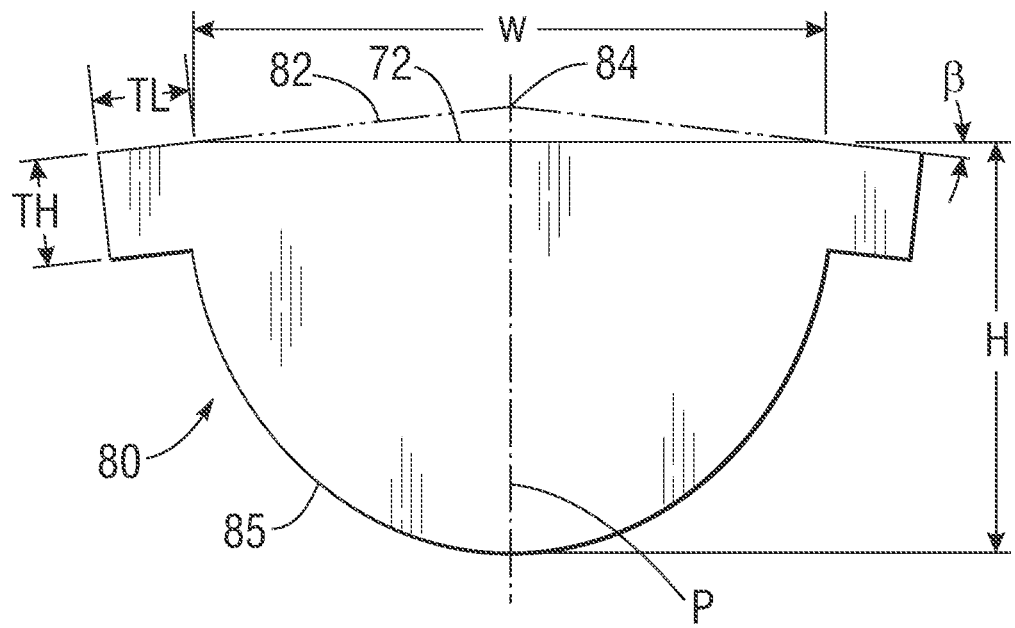
FIG. 10 is a plan view of a flexible leaflet having various dimensions noted for use in describing preferred leaflets.

FIG. 10 is a plan view of a flexible leaflet 80 as in FIG. 8 with various dimensions noted for use in describing preferred leaflets. In particular, the leaflet has a central plane of symmetry P that passes through the apex 84 of the free edge 82. It should be noted that the triangular strip above between the free edge 72 of a conventional leaflet and the free edge 82 of the modified leaflet is shown in phantom to illustrate the difference. The effective height H of the leaflet is shown from a lower central point on the cusp edge 85 to the horizontal line extending across the leaflet between the side tabs (coincident with the free edge 72 of a conventional leaflet). The effective width W of the leaflet extends between the side tabs. The effective area defined by H and W is the area (minus a small edge strip outside of fastening sutures) of the leaflet that experiences tensile stresses from fluid flow through the valve. The side tabs have a length TL, a height TH, and the tabs are offset by an angle β from the horizontal.

In a preferred embodiment, the angle β is between 10-20°, the side tab length TL is about 0.20 inches, and the side tab height TH about 0.20 inches. The effective height H is between about 0.50 inches and 0.90 inches (1.27-2.29 cm), and the effective width W is between about 0.73 inches and 1.20 inches (1.85-3.05 cm). The effective height H and effective width W start small for small valves/leaflets and get larger. Valve sizes range from 19 mm to 33 mm orifices. Therefore, for example, the low end of 0.050 inches of the effective height H is paired with the low end of 0.073 inches of the effective width W for 19 mm valves. The thickness of the tissues used is desirably between 0.014-0.025 inches (0.36-0.64 mm).

FIG. 11 is a top plan view of a heart valve 90 having three of the flexible leaflets 52 shown in FIG. 6A in the closed position illustrating a reduced central aperture 92. Each leaflet free edge 62 includes the aforementioned contoured shape that helps reduce regurgitation. Namely, the free edges 62 each have a pointed apex 68 that coapt and help reduce the size of the aperture 92.

FIG. 12 is a plan view of a flexible leaflet 70 of a conventional prosthetic valve (such as in FIG. 6B) with the flexible leaflet 52 of FIG. 6A superimposed in phantom thereover, by way of direct comparison of the modified shape. The free edge 62 having the apex 68 is shown above the relatively straight free edge 72 of the prior art leaflet. The profile of the free edge 62 diverges above the straight free edge 72 just inward from side tabs 73 such that the modified leaflet 52 is taller. An extra strip of leaflet material 100 continues to the apex 68 and enhances coaptation between the three leaflet free edges. This strip of material 100 extends approximately between the two side tabs 73 and above a line that connects the upper corners 102 of the tabs. The strip 100 gradually widens as it progresses inward from the tabs until it forms a plateau for a majority of its length, then the strip rapidly widens in converging curves that lead to the apex 68.

The modified leaflet 52 further includes an enlarged cusp region as indicated by a series of radii. In the left quadrant, three radii $r_1, r_2, r_3$ indicate the curvature of the conventional leaflet cusp edge 104 as measured from a point 106 at the intersection of the plane of symmetry 108 and a line 110 that connect the lower corners 112 of the side tabs 73. The cusp edge 104 defines a complex curve whose radii changes. In general, $r_1$ and $r_2$ are greater than $r_3$. The right quadrant shows three radii $R_1, R_2, R_3$ that indicate the curvature of the modified leaflet cusp edge 60. The overall height of the two leaflets remains approximately the same, as shown by the convergent radii $r_3$ and $R_3$ at the lower midplane 108, and the width from tab-to-tab is also the same. However, the sides of the modified cusp edge 60, especially in the middle of the quadrant at $R_2$, are enlarged from the conventional leaflet. The complex curve of the modified cusp edge 60 has its smallest radius on the central midplane 108 and gradually increases away from the central plane until it reaches a maximum at about 45° angle from the central midplane, and then gradually decreases to two corners where the two ends of the arcuate cusp edge meet the attachment tabs 73. In a preferred embodiment, $R_2 \geq 1.1\ r_2$, and $R_1 \geq 1.05\ r_1$. Stated another way, the radii of points along the modified arcuate cusp edge are greater than equivalent points along a conventional leaflet; up to 10% greater. At the same time, the radius at the central midplane remains the same as does the radius at the lower corners 112 of the leaflet tabs 73. The modified cusp edge 60 thus gradually diverges larger from the conventional cusp edge from the tab corner 112 to a point about 45° toward the midplane 108, and then gradually converges until the lowermost point at the midplane where the radii are equal. It should also be noted that the separate leaflets for various sizes of heart valves have different absolute values, and the relative increases of the modified leaflet radii can be applied across the spectrum of leaflets.

The enlarged cusp edge 60 as described with respect to FIG. 12 permits the leaflet to move farther out of the flow path when the valve opens, thus reducing the pressure gradient through the valve. The cusp edge enlargement described above is relative to a conventional leaflet mounted on a wireform that has a particular shape, primarily an elliptical cusp shape. It should be understood, and will be explained further below, that the cusp shape of the wireform may be other than elliptical, and therefore the precise contours of the modified leaflet 52 will be enlarged relative to whatever is the conventional shape.

Figure 13A:
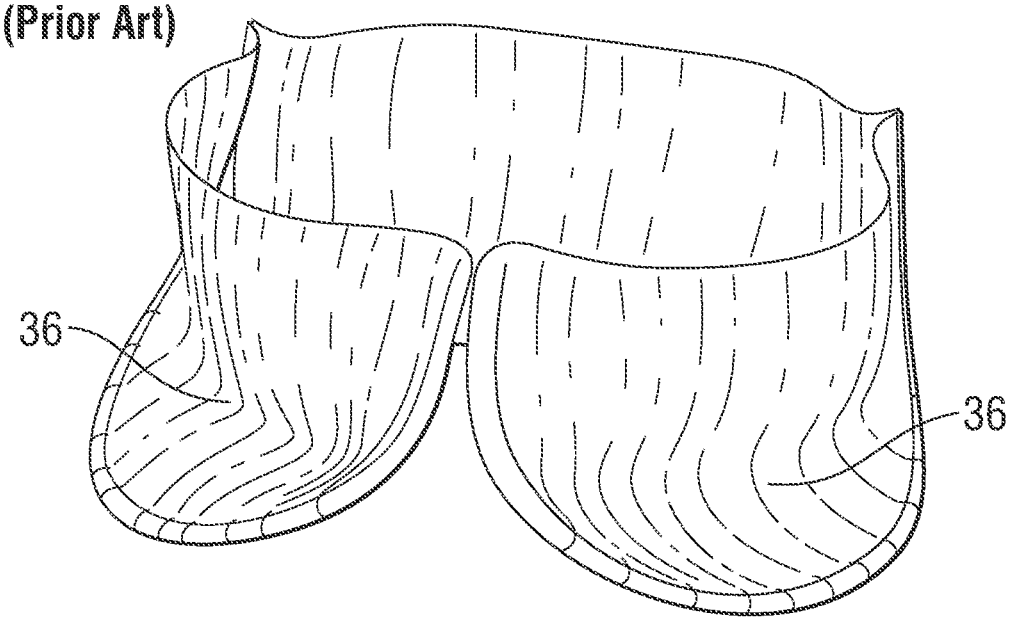
Figure 13B:
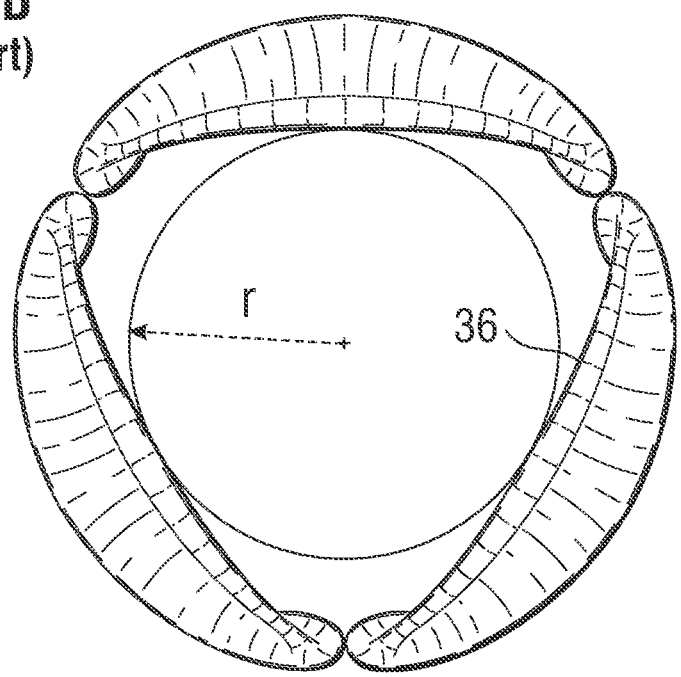
FIG. 13B shows the leaflets in plan view from the outflow end indicating a flow orifice formed thereby.
Figure 14:
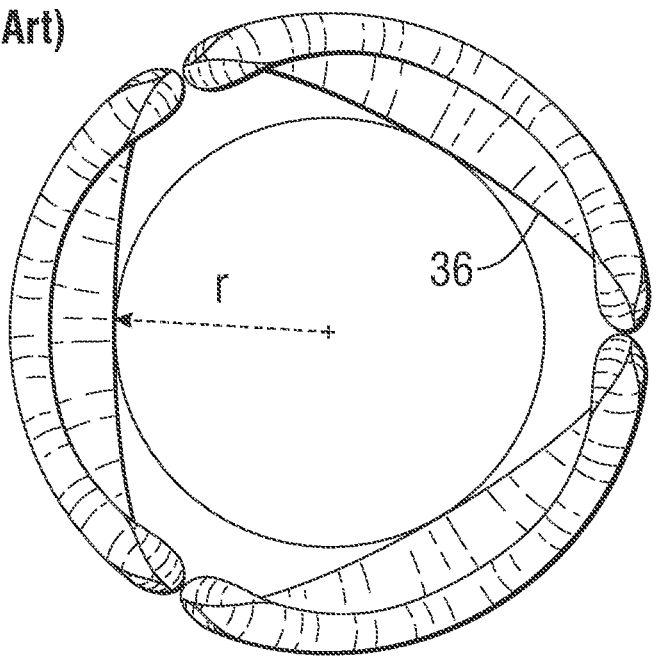
FIG. 14 is a plan view from the inflow end of the flexible leaflets of FIG. 13A indicating the flow orifice formed thereby.

To better illustrate the benefit from altering the leaflet cusp edge shape, FIGS. 13A/13B and 14 show isolated flexible tri-leaflets of a bioprosthetic heart valve of the prior art in the open position. As also shown above in FIGS. 1A and B, typical valves of the prior art have excess material that sags somewhat inward when the valve is open to form a crease or shelf 36 near its mid-point. These shelves 36 extend inward beyond a generally circular orifice defined at the inflow end. A circular orifice created by the inward shelves 36 is seen by the circle having a radius r in FIGS. 13B and 14. Though some flow occurs outside of this circle, it represents an effective orifice area for the purpose of comparison with leaflets of the present application.

Figure 15:
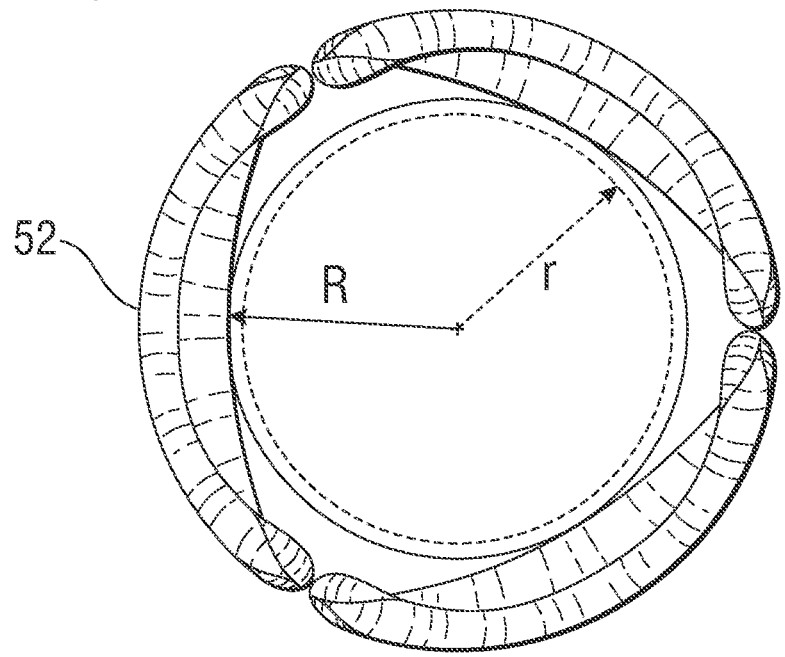
FIG. 15 is a plan view from the inflow end of flexible leaflets of the present application showing an increased flow orifice formed thereby.

FIG. 15 is a plan view from the inflow end of open flexible leaflets 52 of the present application showing an increased flow orifice formed thereby, as indicated by the circle having radius R, with the smaller orifice circle r of the prior art shown in comparison. A small increase in this orifice radius corresponds to a relatively large orifice area increase, and a reduced flow gradient. For example, an increased flow orifice radius from 10 to 10.5 mm, a 5% increase (and orifice diameter increase of only 1 mm), results in an effective flow orifice area increase of from 314 mm$^2$ to 346 mm$^2$, more than a 10% increase. The benefits of reducing the inward shelf or pocket of the leaflets is therefore quite apparent.

FIG. 16A illustrates a wireform or support frame 120 for bioprosthetic heart valves of the prior art. The support frame 120 desirably comprises a single rod-like element generally circumscribing a slight cone with an axially undulating shape defined by alternating inflow cusp regions 122 and outflow commissure regions 124. The arcuate cusp regions 122 have large radii of curvatures relative to the upstanding commissure regions 124, the latter of which terminate at tips 126. The support frame 120 preferably comprises an elongated rod- or wire-like member made out of an elastic biocompatible metal and/or plastic alloy, such as Elgiloy®, Nitinol, polypropylene, etc. The support frame 120 may be bent into the illustrated shape, using conventional wire-forming techniques, with two free ends being joined by a tubular crimp along a relatively straight section extending up one of the commissure regions 124. The material selected for the support frame 120 should be elastic to permit flexing along its length, but should possess a minimum of stiffness to avoid asymmetric deformation of a valve constructed therewith. The commissure regions 124 are cantilevered in an outflow direction and provide support to the flexible leaflets that attach thereto so that the leaflets do not invert from fluid backflow pressure.

FIG. 16B is a radial sectional view through one commissure region 124 of the support frame 120 showing an inward angle γ thereof. This angle corresponds to the same angle as shown in FIG. 2 in a constructed valve, and creates an inward cone of rotation toward the outflow end of the support frame 120. Again, this structure has been used for many years to ensure coaptation of the flexible leaflets.

FIG. 17A is a perspective view of a modified wireform or support frame 130 for a bioprosthetic heart valve of the present application which comprises a single element generally circumscribing a slight cone with an undulating shape defined by alternating inflow cusp regions 132 and outflow commissure regions 134. The arcuate cusp regions 132 have large radii of curvatures relative to the upstanding commissure regions 134, each of which terminate at a tip 136. The support frame 130 preferably comprises an elongated rod- or wire-like member made out of an elastic biocompatible metal and/or plastic alloy, such as Elgiloy®, Nitinol, polypropylene, etc. Again, the support frame 130 may be bent into the illustrated shape, using conventional wire-forming techniques, with two free ends being joined by a tubular crimp 138 along a relatively straight section extending up one of the commissure regions 134. FIG. 17B is a radial sectional view through one commissure region 134 of the support frame showing the outward tilt by an angle α similar to FIG. 5. The wireform structure defines the peripheral contours of the outflow end of the constructed heart valve, and thus defines the flow orifice at the outflow end.

Figure 18A:
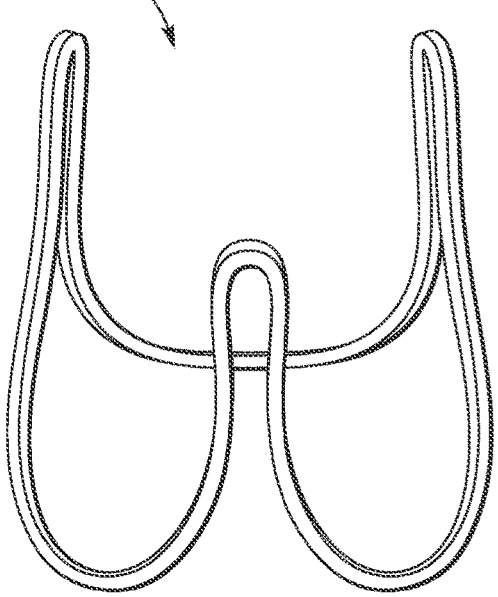
FIGS. 18A and 18B are contracted and expanded views of an exemplary Nitinol support frame for use with heart valves of the present application.
Figure 18B:
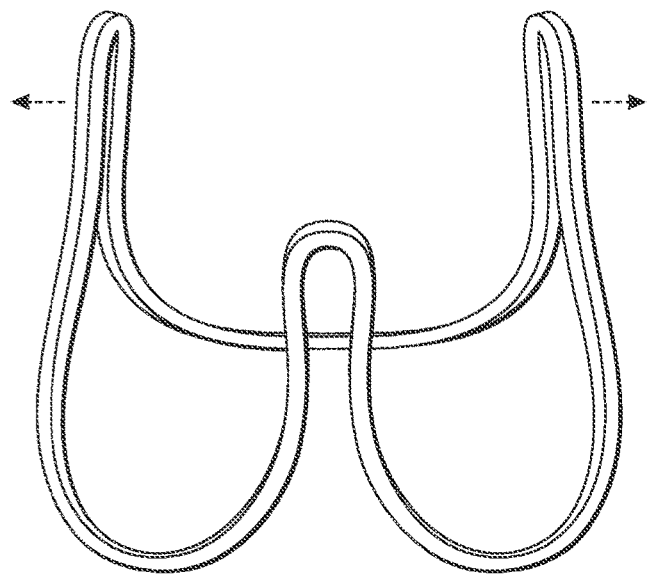

FIGS. 18A and 18B are contracted and expanded views of an exemplary Nitinol support frame 140 for use with heart valves of the present application. In this version, there is no need for a crimp as in the embodiment of FIGS. 17A/17B, and instead the Nitinol frame is cut from a flat sheet and then shape set into the three-dimensional profile shown. More details of the support frame 140 can be found in concurrently filed U.S. Pat. No. 8,986,374, filed May 10, 2010, entitled PROSTHETIC HEART VALVE, the contents of which are incorporated by reference herein.

Figure 19A:
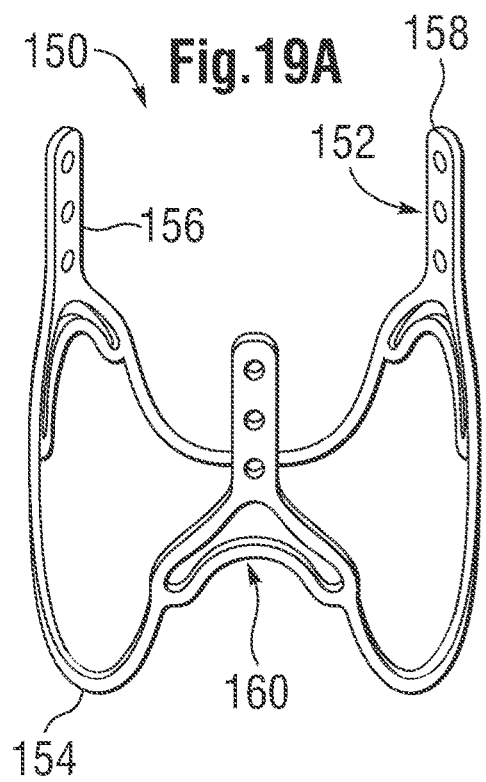
FIGS. 19A and 19B are contracted and expanded views of an alternative Nitinol support frame for use with heart valves of the present application.
Figure 19B:
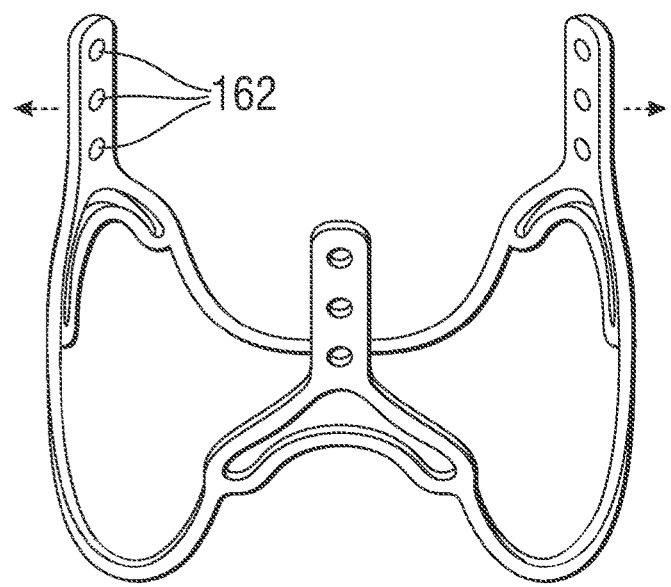

FIGS. 19A and 19B are contracted and expanded views of an alternative Nitinol support frame 150 for use with heart valves of the present application. The support frame 150, as before, defines an undulating periphery of alternating commissure regions 152 and cusps 154. However, while the cusps 154 are relatively unchanged, the commissure regions 152 each include an upstanding bar 156 terminating at a commissure tip 158 that joins to the cusps via an open triangular junction 160. The bars 156 each include a series of through holes 162 that provide anchor points to which the leaflet tabs or intermediate fabric may be sutured. This support frame 150 may be assembled with other internal stent structures, such as shown above at 66 in FIG. 5, or may be covered with fabric and assembled to just the leaflets and sewing ring.

FIG. 20 schematically shows blood flow through a prosthetic heart valve 170 of the prior art that constricts and creates turbulent flow. For purpose of illustration, the valve sits in an aortic annulus between the left ventricle LV and the ascending aorta AA. The valve 170 is shown schematically as an orifice 172 defined at an inflow end and a converging conical outflow end 174 that represents the commissure posts and leaflets in their open state. Because the outflow orifice is smaller than the inflow orifice, flow is compressed through the valve 170 resulting in turbulence, eddies, and a first pressure gradient.

In contrast, FIG. 21 schematically shows blood flow through a prosthetic heart valve 180 of the present application that expands and creates laminar, low gradient flow. Again, the valve 180 mounts in the aortic annulus between the left ventricle LV and the ascending aorta AA. The inflow end 182 defines an orifice similar to the conventional valve shown in FIG. 20, but the outflow end 184 diverges away from the central flow axis, thus enabling blood to flow relatively unimpeded therethrough. The resulting flow lines indicate laminar flow, and the pressure gradient is reduced from the first pressure gradient noted above.

Figure 22:
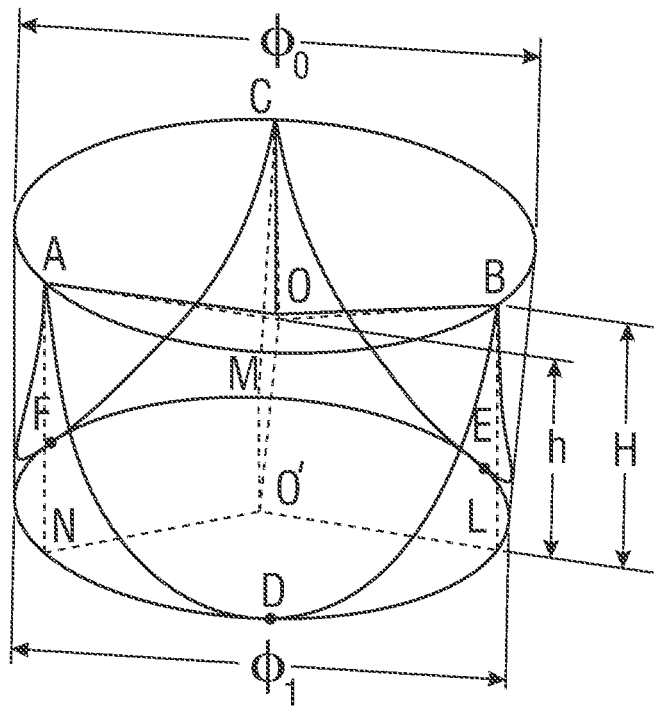
FIG. 22 is a perspective view of a geometric framework of a tri-leaflet prosthetic heart valve with important dimensions and points labeled.

FIG. 22 is a perspective view of a geometric framework of a tri-leaflet prosthetic heart valve with important dimensions and points labeled. The nomenclature is as follows:

A, B, C=leaflet-commissure junctions where leaflets are attached to the commissure strut of the support structure, define outflow plane ABC and outflow circle of relaxed commissure tips D, E, F=cuspal points where the leaflets meet the support structure at the most proximal position to the inflow of the prosthesis (the nadir of the cusps), define inflow plane and annulus circle DEF L, M, N=projections of the commissure points on the inflow annulus circle DEF O=coaptation point or triple point junction where all three leaflets meet upon valve closing O'=projection of the coaptation point on the inflow plane DEF $\Phi_o$=outflow diameter on the circle ABC $\Phi_i$=inflow diameter on the circle DEF H=valve commissure height from plane DEF to plane ABC h=coaptation height from plane DEF to elevation of coaptation point O AOBD=leaflet #1

BOCE=leaflet #2

AOCF=leaflet #3

Typically, the pericardial leaflets are precut from a flat pericardial tissue sheet and are sewn together to form the tri-leaflet design with the dimensional framework shown in FIG. 22. The characteristic dimensions for any tri-leaflet design should include inflow diameter, and the valve height, h. In addition, for most conventional valve designs, the outflow diameter is less than the inflow diameter. To describe the low gradient valve design, we shall introduce a new variable, the relaxation angle, α.

$$\alpha = \tan^{-1}\frac{\Phi_o}{\Phi_i}$$

For the low gradient valve design, the optimal angle is α=4±3°. As comparison, for conventional valves, α=−10°. For low profile pericardial valve design, it is found the best range for the valve height is:

$$\frac{H}{\Phi_i} = 0.5 \pm .1$$

The coaptation height is:

$$\frac{h}{H} = 0.7 \pm .1$$

Figure 23:
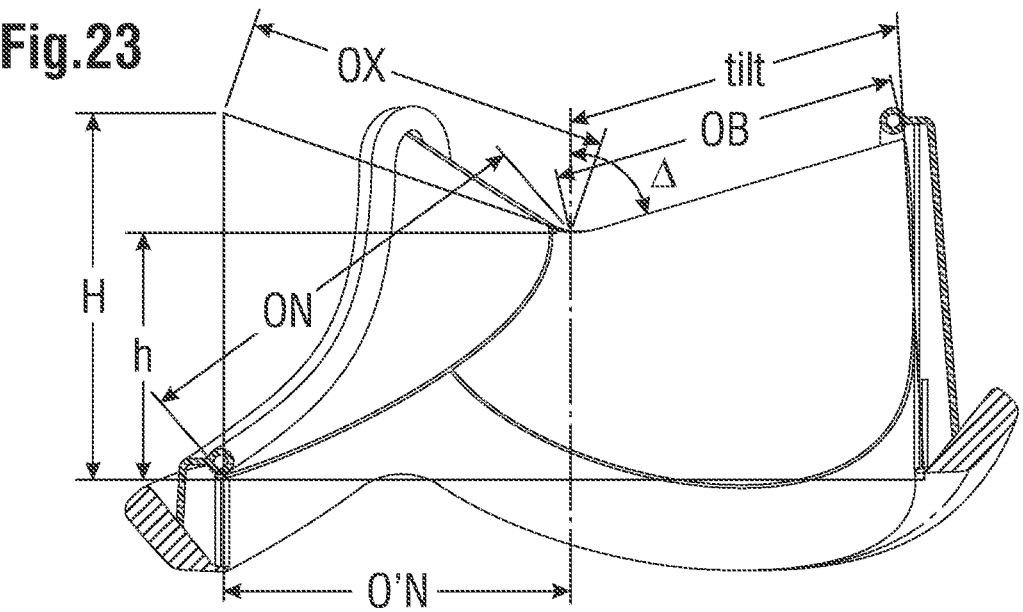
FIG. 23 is a perspective sectional view through a tri-leaflet prosthetic heart valve described herein with important dimensions and angles labeled.

FIG. 23 is a perspective sectional view through a tri-leaflet prosthetic heart valve described herein with important dimensions and angles labeled. The optimal leaflet shape is closely related to the leaflet attachment line on the orifice supporting structure. Known orifice support structures, or wireforms, are defined by cusps having an elliptical curve and a linear segment. For the present application, the leaflet also desirably has a corresponding elliptical cuspal segment and a corresponding linear segment.

Figure 24A:
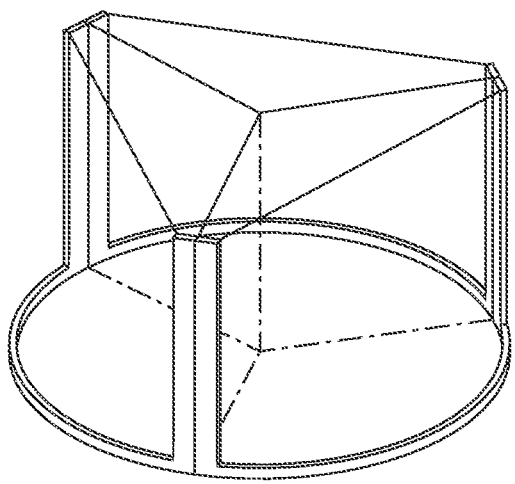
FIGS. 24A/24B, 25A/25B, 26A/26B, and 27A/27B are perspective and elevational views, respectively, of the geometry of alternative support frames for tri-leaflet prosthetic heart valves whose shapes may be customized in accordance with the principles described herein to produce low gradient flow.
Figure 24B:
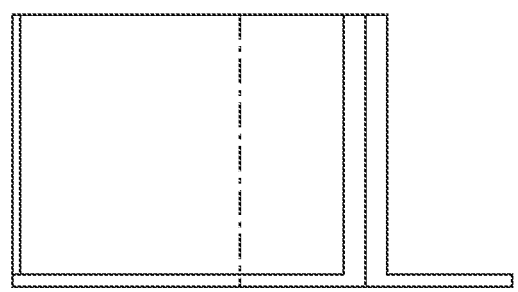
Figure 25A:
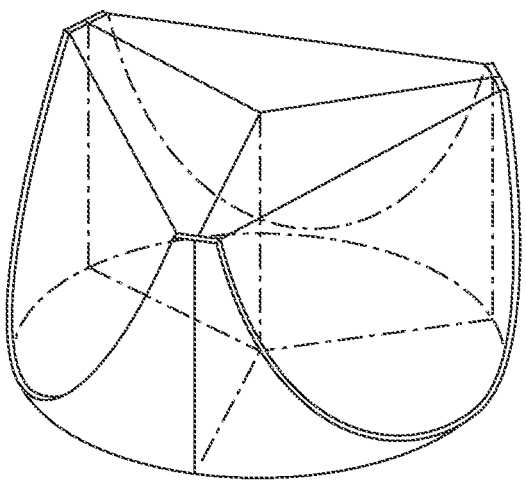
Figure 25B:
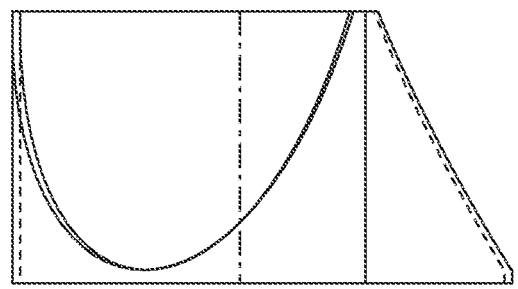
Figure 26A:
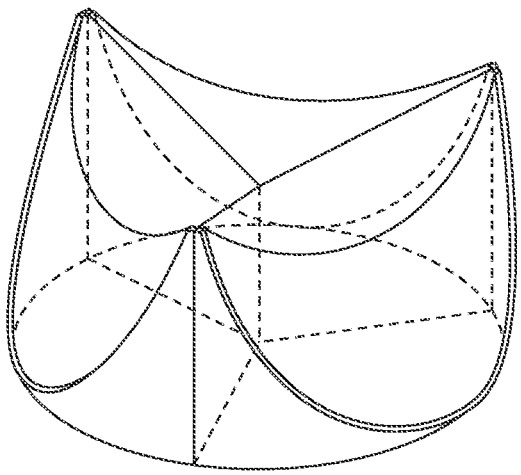
Figure 26B:
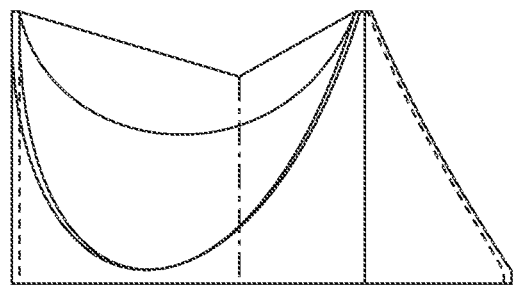
Figure 27A:
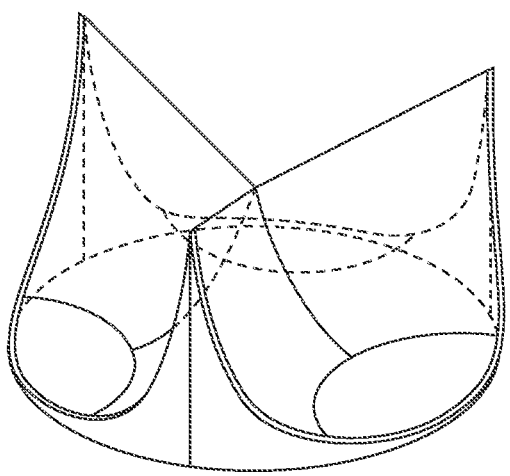
Figure 27B:
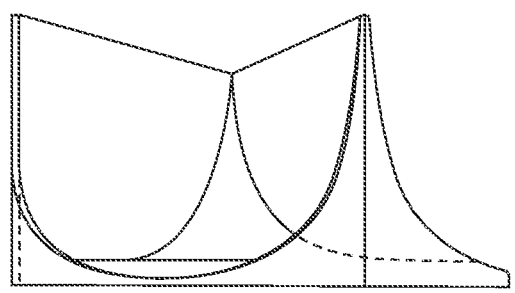

Though a classic elliptical-linear cusp shape is desired, other shapes may be used. For instance, FIGS. 24A/24B, 25A/25B, 26A/26B, and 27A/27B are perspective and elevational views, respectively, of the geometry of alternative support frames for tri-leaflet prosthetic heart valves whose shapes may be customized in accordance with the principles described herein to produce low gradient flow. For instance, in FIGS. 24A/24B the leaflet is a rectangular shape and the wireform is a corresponding cutout from a cylindrical or conical surface. Such a shape may not be optimum, but the leaflets shape can be modified so that the gradient is minimized.

While the invention has been described in its preferred embodiments, it is to be understood that the words which have been used are words of description and not of limitation. Therefore, changes may be made within the appended claims without departing from the true scope of the invention.

What is claimed is:

1. A low pressure gradient prosthetic heart valve, comprising:
   a support frame including a leaflet attachment edge with an undulating shape defined by alternating arcuate inflow cusp regions and on an inflow end and arcuate outflow commissure posts on an outflow end, the support frame, in a relaxed state, circumscribing a flow volume having a central axis, the flow volume having a maximum flow orifice area perpendicular to the central axis limited by the inflow end of the support frame; and
   a plurality of flexible bovine pericardial leaflets attached to the support frame and extending inward toward the axis, each leaflet having an arcuate cusp edge with no straight portions opposite a free edge and opposed attachment tabs therebetween, wherein the cusp edge conforms to a corresponding support frame cusp region and attaches therealong between adjacent commissure posts, and a free edge that coapts with the free edges of the other leaflets to provide one way flow through the valve, wherein the cusp edge is defined by a complex curve of multiple radii;
   wherein when the valve opens the free edges of the leaflets move outward toward the support frame from fluid flow in an outflow direction and corresponding fluid pressures, and wherein each leaflet has a size and is attached to the corresponding support frame cusp region such that when the valve opens the leaflets spread outward to provide an outflow orifice area that is no less than the maximum flow orifice area.

2. The heart valve of claim 1, wherein each leaflet is symmetric about a central midplane, and the complex curve of the cusp edge has a radius that is smallest on the central midplane, gradually increases on both sides away from the central plane, reaches a maximum radius at about 45° angle from the central axis, and then gradually decreases to two corners where the cusp edge meets the attachment tabs.

3. The heart valve of claim 2, wherein the free edge has a strip above a straight line drawn between the attachment tabs forming a plateau for a majority of a length of the strip.

4. The heart valve of claim 1, wherein each commissure post of the support frame, in the relaxed state, is angled radially outward so as to provide an outflow orifice area greater than the maximum flow orifice area.

5. The heart valve of claim 4, wherein the radially outward angle made by each commissure post is α=4±3°.

6. The heart valve of claim 4, further including a suture-permeable sewing ring surrounding the cusp regions that provides a structural anchor to the surrounding anatomy at an inflow end of the support frame, wherein the commissure posts are cantilevered toward an outflow direction from the cusp regions when anchored to the surrounding anatomy such that the commissure tips may flex radially in and out from forces associated with fluid pressures on the flexible leaflets.

7. The heart valve of claim 1, wherein the support frame comprises an elongated rod-like member made out of an elastic material.

8. The heart valve of claim 7, wherein the support frame is formed as a continuous piece of Nitinol with no breaks or crimp.

9. The heart valve of claim 1, wherein the commissure posts of the support frame each include an upstanding bar and a series of through holes therein that provide anchor points for other elements of the heart valve.

10. The heart valve of claim 1, wherein the arcuate cusp regions have large radii of curvatures relative to the commissure posts so that the commissure posts commence at adjacent relatively straight sections leading up to an arcuate commissure tip, and the cusp edges of the leaflets attach along a line that follows the arcuate cusp regions and along the relatively straight sections of the commissure posts.

11. A low pressure gradient prosthetic heart valve, comprising:
- a support frame including a leaflet attachment edge with an undulating shape defined by alternating arcuate inflow cusp regions and on an inflow end and arcuate outflow commissure posts on an outflow end, the support frame, in a relaxed state, circumscribing a flow volume having a central axis, the flow volume having a maximum flow orifice area perpendicular to the central axis limited by the inflow end of the support frame; and
- a plurality of flexible bovine pericardial leaflets attached to the support frame and extending inward toward the axis, each leaflet having an arcuate cusp edge with no straight portions opposite a free edge and opposed attachment tabs therebetween, wherein the cusp edge conforms to a corresponding support frame cusp region and attaches therealong between adjacent commissure posts, and a free edge that coapts with the free edges of the other leaflets to provide one way flow through the valve, each leaflet being symmetric about a central midplane and wherein the free edge diverges above a straight line perpendicular to the central midplane drawn between the attachment tabs to form a supplemental strip of leaflet material that widens as it progresses inward from the attachment tabs and has an apex on the vertical midplane;

wherein when the valve opens the free edges of the leaflets move outward toward the support frame from fluid flow in an outflow direction and corresponding fluid pressures, and the supplemental strip of leaflet material and apex of the coapting free edges help close any aperture that naturally forms between the three leaflets along the flow axis, thus reducing regurgitation.

12. The heart valve of claim 11, wherein the free edge of each leaflet gradually widens as it progresses inward from the tabs until it forms a plateau for a majority of a length of the strip, and then rapidly widens in converging curves that lead to the apex.

13. The heart valve of claim 11, wherein the cusp edge of each leaflet is defined by a complex curve of multiple radii, and wherein each leaflet has a size and is attached to the corresponding support frame cusp region such that when the valve opens the leaflets spread outward to provide an outflow orifice area that is no less than the maximum flow orifice area.

14. The heart valve of claim 13, wherein the complex curve of the cusp edge has a radius that is smallest on the central midplane, gradually increases on both sides away from the central plane, reaches a maximum radius at about 45° angle from the central axis, and then gradually decreases to two corners where the cusp edge meets the attachment tabs.

15. The heart valve of claim 11, wherein each commissure post of the support frame, in the relaxed state, is angled radially outward so as to provide an outflow orifice area greater than the maximum flow orifice area.

16. The heart valve of claim 15, wherein the radially outward angle made by each commissure post is $\alpha=4°\pm3°$.

17. The heart valve of claim 15, further including a suture-permeable sewing ring surrounding the cusp regions that provides a structural anchor to the surrounding anatomy at an inflow end of the support frame, wherein the commissure posts are cantilevered toward an outflow direction from the cusp regions when anchored to the surrounding anatomy such that the commissure tips may flex radially in and out from forces associated with fluid pressures on the flexible leaflets.

18. The heart valve of claim 11, wherein the support frame comprises an elongated rod-like member made out of an elastic material.

19. The heart valve of claim 18, wherein the support frame is formed as a continuous piece of Nitinol with no breaks or crimp.

20. The heart valve of claim 11, wherein the commissure posts of the support frame each include an upstanding bar and a series of through holes therein that provide anchor points for other elements of the heart valve.

* * * * *